United States Patent
Wu et al.

(10) Patent No.: US 12,198,400 B2
(45) Date of Patent: *Jan. 14, 2025

(54) PROVIDING EMOTIONAL CARE IN A SESSION

(71) Applicant: Microsoft Technology Licensing, LLC, Redmond, WA (US)

(72) Inventors: Xianchao Wu, Tokyo (JP); Daigo Hamura, Bellevue, WA (US); Yongdong Wang, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/373,583

(22) Filed: Sep. 27, 2023

(65) Prior Publication Data

US 2024/0020942 A1    Jan. 18, 2024

Related U.S. Application Data

(63) Continuation of application No. 17/752,149, filed on May 24, 2022, now Pat. No. 11,810,337, which is a (Continued)

(51) Int. Cl.
*G06F 40/35* (2020.01)
*A61B 5/16* (2006.01)
(Continued)

(52) U.S. Cl.
CPC ............ *G06V 10/454* (2022.01); *A61B 5/165* (2013.01); *G06F 40/35* (2020.01); *G06F 40/56* (2020.01); *G06N 3/04* (2013.01); *G06V 10/764* (2022.01)

(58) Field of Classification Search
CPC .......... G06F 40/35; G06F 40/56; A61B 5/165
(Continued)

(56) References Cited

U.S. PATENT DOCUMENTS

2008/0096533 A1* 4/2008 Manfredi ............... G06N 3/006
                                                                          455/412.1
2017/0364504 A1* 12/2017 Dandapat .............. G06F 40/279
(Continued)

OTHER PUBLICATIONS

Starr Roxanne Hiltz; Murray Turoff, "Social and Psychological Processes in Computerized Conferencing," in The Network Nation: Human Communication via Computer , MIT Press, 1993, pp. 76-127. (Year: 1993) (Year: 1993).*
(Continued)

*Primary Examiner* — Bharatkumar S Shah
(74) *Attorney, Agent, or Firm* — Schwegman Lundberg & Woessner, P.A.

(57) ABSTRACT

A method and apparatus for providing emotional care in a session between a user and conversational agent. A first group of images comprising one or more images associated with the user may be received in the session. A user profile may be obtained. A first group of textual descriptions may be generated from the first group of images based at least on emotion information in the user profile. A first memory record may be created based at least on the first group of images and the first group of textual descriptions. A second group of images may be received in the session to generate a second group of textual descriptions from the second group of images based at least on the emotion information in the user profile. A second memory record may be created based at least on the second group of images and the second group of textual descriptions.

20 Claims, 20 Drawing Sheets

Related U.S. Application Data continuation of application No. 16/769,987, filed as application No. PCT/CN2018/071354 on Jan. 4, 2018, now Pat. No. 11,369,297.

(51) Int. Cl.
*G06F 40/56* (2020.01)
*G06N 3/04* (2023.01)
*G06V 10/44* (2022.01)
*G06V 10/764* (2022.01)

(58) Field of Classification Search
USPC .......................................................... 704/9
See application file for complete search history.

(56) References Cited

U.S. PATENT DOCUMENTS

2017/0364741 A1* 12/2017 Hau .................... G06V 10/768
2019/0239795 A1* 8/2019 Kotake ................ A61B 5/7267

OTHER PUBLICATIONS

K.-J. Oh, D. Lee, B. Ko and H.-J. Choi, "A Chatbot for Psychiatric Counseling in Mental Healthcare Service Based on Emotional Dialogue Analysis and Sentence Generation," 2017 18th IEEE International Conference on Mobile Data Management (MDM), Daejeon, Korea (South), 2017, pp. 371-375, doi: 10.1109/ (Year: 2017).*

* cited by examiner

PROVIDING EMOTIONAL CARE IN A SESSION

CROSS-REFERENCE TO RELATED APPLICATION

This application is a continuation of U.S. patent application Ser. No. 17/752,149, filed May 24, 2022, which application is a continuation of U.S. patent application Ser. No. 16/769,987 filed on Jun. 4, 2020, now issued as U.S. Pat. No. 11,369,297, on Jun. 28, 2022, which is a U.S. National Stage Filing under 35 U.S.C. 371 of International Patent Application Serial No. PCT/CN2018/071354, filed Jan. 4, 2018, and published as WO2019/134091 A1 on Jul. 11, 2019, which applications and publications are incorporated herein by reference in their entirety.

BACKGROUND

Artificial Intelligence (AI) chatbot is becoming more and more popular, and is being applied in an increasing number of scenarios. The chatbot is designed to simulate people's conversation, and may chat with users by text, speech, image, etc. Generally, the chatbot may scan for keywords within a message input by a user or apply natural language processing on the message, and provide a response with the most matching keywords or the most similar wording pattern to the user.

SUMMARY

This Summary is provided to introduce a selection of concepts that are further described below in the Detailed Description. It is not intended to identify key features or essential features of the claimed subject matter, nor is it intended to be used to limit the scope of the claimed subject matter.

Embodiments of the present disclosure propose method and apparatus for providing emotional care in a session between a user and an electronic conversational agent. A first group of images may be received in the session, the first group of images comprising one or more images associated with the user. A user profile of the user may be obtained. A first group of textual descriptions may be generated from the first group of images based at least on emotion information in the user profile. A first memory record may be created based at least on the first group of images and the first group of textual descriptions.

It should be noted that the above one or more aspects comprise the features hereinafter fully described and particularly pointed out in the claims. The following description and the drawings set forth in detail certain illustrative features of the one or more aspects. These features are only indicative of the various ways in which the principles of various aspects may be employed, and this disclosure is intended to include all such aspects and their equivalents.

BRIEF DESCRIPTION OF THE DRAWINGS

The disclosed aspects will hereinafter be described in connection with the appended drawings that are provided to illustrate and not to limit the disclosed aspects.

DETAILED DESCRIPTION

The present disclosure will now be discussed with reference to several example implementations. It is to be understood that these implementations are discussed only for enabling those skilled in the art to better understand and thus implement the embodiments of the present disclosure, rather than suggesting any limitations on the scope of the present disclosure.

Following the developing of medical techniques and better living environments, people's average life-time is extended significantly in the recent decades. Taking Japan as an example, the average life-time of men/women is around 83 to 84 years old. In addition, there are more than 25% people in Japan who are over 65 years old. Many other countries will follow the same trend in the near future. One challenge for these old people is how they can spend 20 or more years after their retirement in a healthy living style.

Embodiments of the present disclosure propose to utilize an electronic conversational agent to provide timely and efficient emotional care to users. The users not only include the old people, but also include other people in various ages. Herein, "emotional care" may refer to emotional communications or assistances provided to a user in various approaches, such as, emotional chatting, providing knowledge related to diseases, foods and medicines, monitoring a psychological or cognitive condition of the user through conducting psychological or cognitive tests, creating and storing memory records for the user, etc. The emotional care provided by the embodiments of the present disclosure would be beneficial for the user to live in a healthy way, especially meeting various emotional requirements of the user.

The electronic conversational agent may provide the emotional care in a session with the user. The electronic conversational agent may be, such as, a chatbot. Conventionally, a chatbot may conduct automated sessions with a user. Herein, "session" may refer to a time-continuous dialog between two chatting participants and may include messages and responses in the dialog, wherein "message" refers to any information input by the user, e.g., queries from the user, answers of the user to questions from the chatbot, opinions of the user, etc., and "response" refers to any information provided by the chatbot, e.g., answers of the chatbot to questions from the user, comments of the chatbot, etc. The term "message" and the term "query" may also be interchangeably used.

Figure 1:
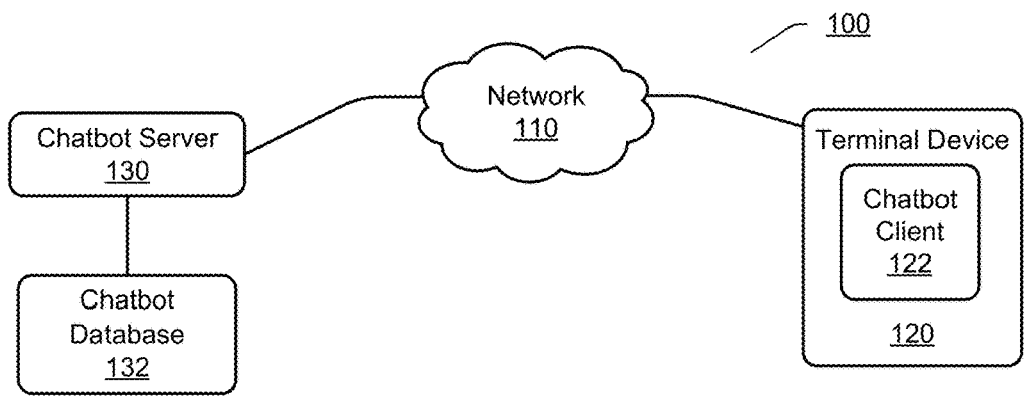
FIG. 1 illustrates an exemplary network architecture deploying a chatbot according to an embodiment.

FIG. 1 illustrates an exemplary network architecture 100 deploying a chatbot according to an embodiment.

In FIG. 1, a network 110 is applied for interconnecting among a terminal device 120 and a chatbot server 130.

The network 110 may be any type of networks capable of interconnecting network entities. The network 110 may be a single network or a combination of various networks. In terms of coverage range, the network 110 may be a Local Area Network (LAN), a Wide Area Network (WAN), etc. In terms of carrying medium, the network 110 may be a wireline network, a wireless network, etc. In terms of data switching techniques, the network 110 may be a circuit switching network, a packet switching network, etc.

The terminal device 120 may be any type of electronic computing devices capable of connecting to the network 110, assessing servers or websites on the network 110, processing data or signals, etc. For example, the terminal device 120 may be desktop computers, laptops, tablets, smart phones, AI terminals, wearable devices, etc. Although only one terminal device is shown in FIG. 1, it should be appreciated that a different number of terminal devices may connect to the network 110. The terminal device 120 may be used by a user.

The terminal device 120 may include a chatbot client 122 which may provide automated chatting service for the user. In some cases, the chatbot client 122 may interact with the chatbot server 130. For example, the chatbot client 122 may transmit messages input by the user to the chatbot server 130, receive responses associated with the messages from the chatbot server 130, and provide the responses to the user. However, it should be appreciated that, in other cases, instead of interacting with the chatbot server 130, the chatbot client 122 may also locally generate responses to messages input by the user.

The chatbot server 130 may connect to or incorporate a chatbot database 132. The chatbot database 132 may comprise information that can be used by the chatbot server 130 for generating responses.

It should be appreciated that all the network entities shown in FIG. 1 are exemplary, and depending on specific application requirements, any other network entities may be involved in the network architecture 100.

Figure 2:
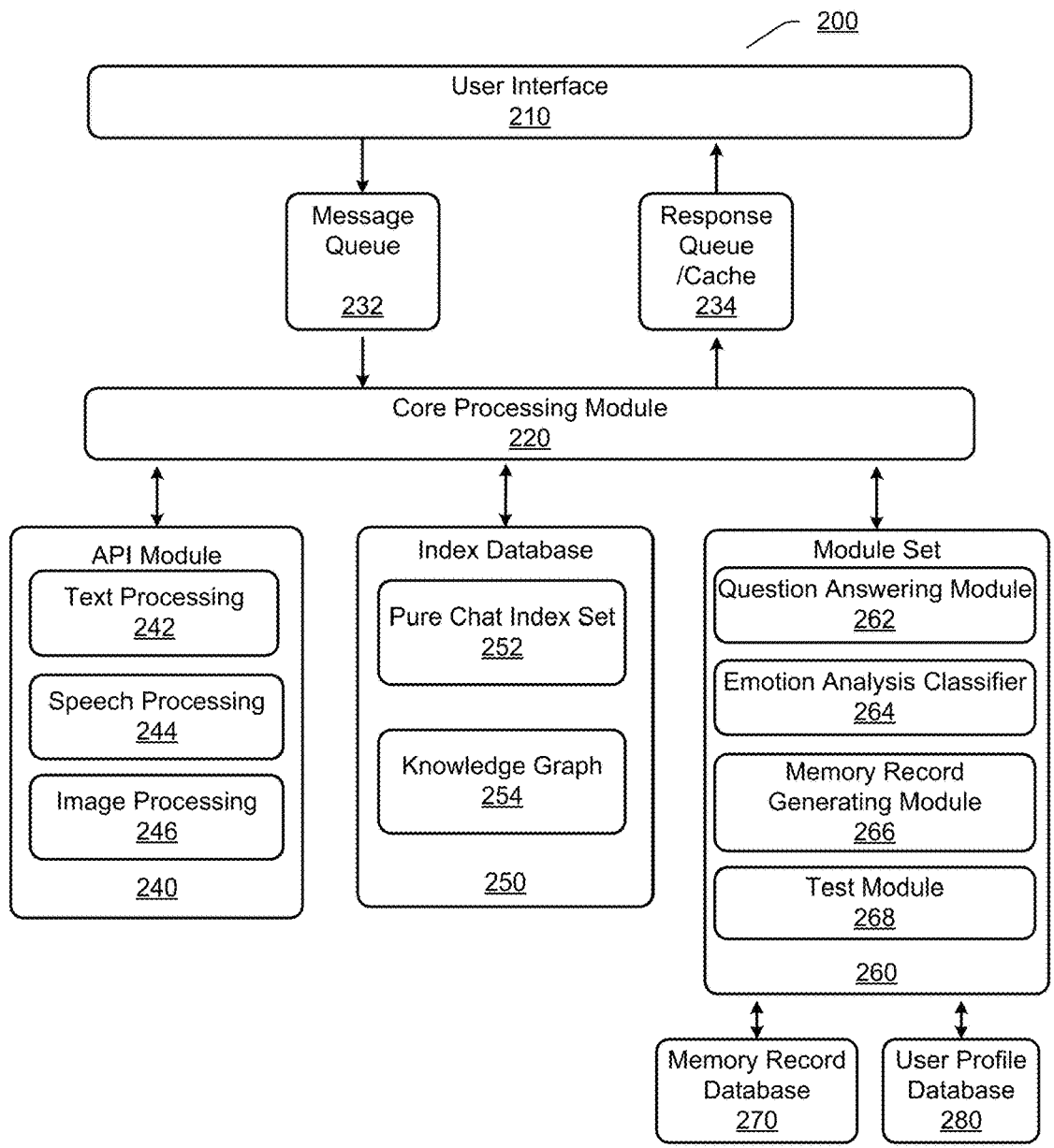
FIG. 2 illustrates an exemplary chatbot system according to an embodiment.

FIG. 2 illustrates an exemplary chatbot system 200 according to an embodiment.

The chatbot system 200 may comprise a user interface (UI) 210 for presenting a chat window. The chat window may be used by the chatbot for interacting with a user.

The chatbot system 200 may comprise a core processing module 220. The core processing module 220 is configured for, during operation of the chatbot, providing processing capabilities through cooperation with other modules of the chatbot system 200.

The core processing module 220 may obtain messages input by the user in the chat window, and store the messages in the message queue 232. The messages may be in various multimedia forms, such as, text, speech, image, video, etc.

The core processing module 220 may process the messages in the message queue 232 in a first-in-first-out manner. The core processing module 220 may invoke processing units in an application program interface (API) module 240 for processing various forms of messages. The API module 240 may comprise a text processing unit 242, a speech processing unit 244, an image processing unit 246, etc.

For a text message, the text processing unit 242 may perform text understanding on the text message, and the core processing module 220 may further determine a text response.

For a speech message, the speech processing unit 244 may perform a speech-to-text conversion on the speech message to obtain text sentences, the text processing unit 242 may perform text understanding on the obtained text sentences, and the core processing module 220 may further determine a text response. If it is determined to provide a response in speech, the speech processing unit 244 may perform a text-to-speech conversion on the text response to generate a corresponding speech response.

For an image message, the image processing unit 246 may perform image recognition on the image message to generate corresponding texts, and the core processing module 220 may further determines a text response. In some cases, the image processing unit 246 may also be used for obtaining an image response based on the text response.

Moreover, although not shown in FIG. 2, the API module 240 may also comprise any other processing units. For example, the API module 240 may comprise a video processing unit for cooperating with the core processing module 220 to process a video message and determine a response.

The core processing module 220 may determine responses through an index database 250. The index database 250 may comprise a plurality of index items that can be retrieved by the core processing module 220 for determining responses.

The index database 250 may comprise a pure chat index set 252. The pure chat index set 252 may comprise index items that are prepared for free chatting between the chatbot and users, and may be established with data from, e.g., social networks. The index items in the pure chat index set 252 may or may not be in a form of question-answer (QA) pair, e.g., <question, answer>. Question-answer pair may also be referred to as message-response pair. In an implementation, the pure chat index set 252 may be established based on topics interested by a user, and thus may be used for providing answers in consideration of the topics interested by the user.

The index database 250 may comprise a knowledge graph 254. Herein, the knowledge graph 254 may refer to a single knowledge graph or a combination of a plurality of knowledge graphs that contains knowledge information related to domains of interest, e.g., diseases, foods, medicines, etc. The knowledge graph 254 may be established based on various public knowledge sources, e.g., public websites on the network, publications, etc. For example, knowledge-style web sites may contain various knowledge records related to domains of interest, and these knowledge records may be used for establishing a knowledge graph related to the domains. This knowledge graph may be continuously extended as more and more knowledge is obtained from the network.

The chatbot system 200 may comprise a module set 260 which is a collection of functional modules that can be implemented for providing emotional care according to the embodiments of the present disclosure.

The module set 260 may comprise a question answering module 262. The question answering module 262 may be configured for performing deep question answering based at least on the pure chat index set 252 and/or the knowledge graph 254. In an implementation, when receiving a question from the user, the question answering module 262 may determine a response based on the pure chat index set 252. In the case that the pure chat index set 252 is established based on the topics interested by the user, the question answering module 262 may provide the response in consideration of the topics interested by the user. In an implementation, when receiving a question from the user, the question answering module 262 may determine a response based on the knowledge graph 254. In the case that the knowledge graph 254 is established based on knowledge information about diseases, foods and/or medicines, the question answering module 262 may provide knowledge about diseases, foods and/or medicines in the response and thus may answer the user's question about diseases, foods and/or medicines. The question answering module 262 may adopt a latent semantic matching algorithm, e.g., a learning-to-rank (LTR) framework with rich latent semantic features, for matching the user's questions with index items in the pure chat index set 252 and/or the knowledge graph 254. The matching is performed in a latent semantic space.

The module set 260 may comprise an emotion analysis classifier 264. The emotion analysis classifier 264 may be configured for performing emotion analysis on text, image, voice, video, etc. For example, when an image is input, the emotion analysis classifier 264 may generate emotion information for the image, e.g., an emotion vector, and thus derive an emotion category for the image.

The module set 260 may comprise a memory record generating module 266. The memory record generating module 266 may be used for creating memory records based on a chat flow between the chatbot and the user. Herein, "memory record" may refer to a record of experiences that are related to the user, including events, persons, locations, times, etc. In an implementation, the memory record generating module 266 may generate textual descriptions from one or more images provided by the user. These images may be various photos that are associated with the user's experiences, such as, photos taken at the time that the user was traveling, the user was getting together with his family or friends, etc. A memory record may be further created by the memory record generating module 266 based on the images and corresponding textual descriptions. For example, if the user uploads a plurality of photos taken when he was visiting a city, a memory record about the user's travel to the city may be created based on these photos and their textual descriptions. This memory record may be created like a "story" about the user's travel to the city. In other words, a memory record is a collection of textual descriptions that are related to the same topic, event etc. Furthermore, the memory record generating module 266 may link two or more memory records together into a joint memory record, thus forming a list of "stories" that have relationship among each other. In response to receiving one or more images from the user in a session, a response which is generated based on a memory record for the images may be returned to the user in the session. Alternatively, memory records may also be stored in a memory record database 270, and may be retrieved and provided later to the user for helping the user to recall what he has experienced in the past. For example, during chatting with the user, after receiving a message from the user, the chatbot may retrieve one or more memory records associated with the message from the memory record database 270 and provide a response based on the retrieved memory records. In this way, the chatbot may help the user to recall or remember his past experiences, thus improving user experiences of the automated chatting service.

The module set 260 may comprise a test module 268. The test module 268 may be used for monitoring the user's psychological or cognitive conditions through, such as, conducting psychological or cognitive tests in a session. The psychological or cognitive tests may be conducted in an explicit way or in an implicit way.

The module set 260 may comprise a user profile database 280. Various personalized information about the user may be stored in the user profile database 280 as a user profile. The user profile may be generated based on session logs between the user and the chatbot. The user profile may comprise basic information about the user, e.g., gender, age, location, etc. The user profile may comprise emotion information associated with the user, which reflects the user's emotions on certain topics. For example, the emotion information in the user profile may comprise topics involved in the session logs of the user, the user's opinions on the topics, and emotion categories of the opinions. An emotion category of an opinion may be obtained through performing emotion analysis on the opinion. The user profile may comprise fact information associated with the user, which reflects various facts talked by the user. For example, the fact information in the use profile may comprise topics, actions of the user, locations, times, etc.

The user profile may be utilized by other modules. In an implementation, the memory record generating module 266 may generate textual description from images based at least on emotion information in the user profile. Thus, the textual description may be generated in an approach which takes the user's emotions into consideration. In an implementation, the test module 268 may determine questions in tests in consideration of topics in the user profile that are interested by the user or most frequently talked by the user.

The core processing module 220 may provide responses to a response queue or response cache 234. For example, the response cache 234 may ensure that a sequence of responses can be displayed in a pre-defined time stream. Assuming that, for a message, there are no less than two responses determined by the core processing module 220, then a time-delay setting for the responses may be necessary. For example, if a message input by the user is "Did you eat your breakfast?", two responses may be determined, such as, a first response "Yes, I ate bread" and a second response "How about you? Still feeling hungry?". In this case, through the response cache 234, the chatbot may ensure that the first response is provided to the user immediately. Further, the chatbot may ensure that the second response is provided in a time delay, such as 1 or 2 seconds, so that the second response will be provided to the user 1 or 2 seconds after the first response. As such, the response cache 234 may manage the to-be-sent responses and appropriate timing for each response.

The responses in the response queue or response cache 234 may be further transferred to the UI 210 such that the responses can be displayed to the user in the chat window.

It should be appreciated that all the elements shown in the chatbot system 200 in FIG. 2 are exemplary, and depending on specific application requirements, any shown elements may be omitted and any other elements may be involved in the chatbot system 200.

Figure 3:
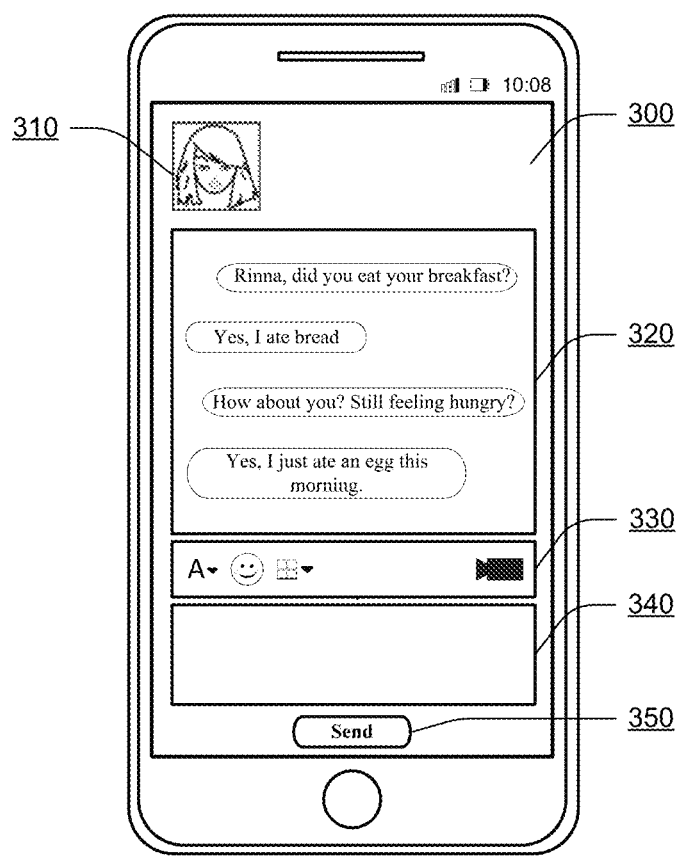
FIG. 3 illustrates an exemplary user interface according to an embodiment.

FIG. 3 illustrates an exemplary user interface 300 according to an embodiment.

The user interface 300 is included in a terminal device, and may comprise a chatbot icon 310, a presentation area 320, a control area 330 and an input area 340. The chatbot icon 310 may be a photo or picture representing the chatbot. The presentation area 320 displays a chat window that contains messages and responses in a session between a user and the chatbot. The control area 330 includes a plurality of virtual buttons for the user to perform message input settings. For example, the user may select to make a voice input, attach image files, select emoji symbols, make a screenshot of the current screen, activate camera, etc. through the control area 330. The input area 340 is used by the user for inputting messages. For example, the user may type text through the input area 340. The user interface 300 may further comprise a virtual button 350 for confirming to send input messages. If the user touches the virtual button 350, the messages input in the input area 340 may be sent to the presentation area 320.

It should be appreciated that all the elements and their layout shown in FIG. 3 are exemplary. Depending on specific application requirements, the user interface in FIG. 3 may omit or add any elements, and the layout of the elements in the user interface in FIG. 3 may also be changed in various approaches. For example, although the messages and responses are shown in a form of text in the presentation area 320, the messages and responses may also be in a form of voice. Accordingly, the chatbot and the user may chat by voices.

As mentioned above, the embodiments of the present disclosure may propose an emotion analysis classifier. The emotion analysis classifier may classify emotion of text, voice, image and video into a respective category. In an implementation, the emotion analysis classifier may be of 8 dimensions and may discriminate 8 categories of emotion, including happiness, anger, fear, contempt, sadness, surprise, disgust and neutrality. It should be appreciated that although the following discussion is related to the emotion analysis classifier with 8 categories of emotion, the embodiments of the present disclosure are not limited to 8 categories of emotion. Instead, emotion analysis classifiers with any other number of emotion categories may be obtained under the concept of the present disclosure.

An exemplary sentence with the emotion "happiness" may be "I'm so glad to hear that!". An exemplary sentence with the emotion "anger" may be "How dare you ignore that!". An exemplary sentence with the emotion "fear" may be "It's a terrible accident". An exemplary sentence with the emotion "contempt" may be "only a computer cannot be that swagger". An exemplary sentence with the emotion "sadness" may be "I don't like it and want to cry". An exemplary sentence with the emotion "surprise" may be "What? Really?". An exemplary sentence with the emotion "disgust" may be "He is more stupid than I expected". An exemplary sentence with the emotion "neutrality" may be "Tomorrow's schedule is determined".

Figure 4:
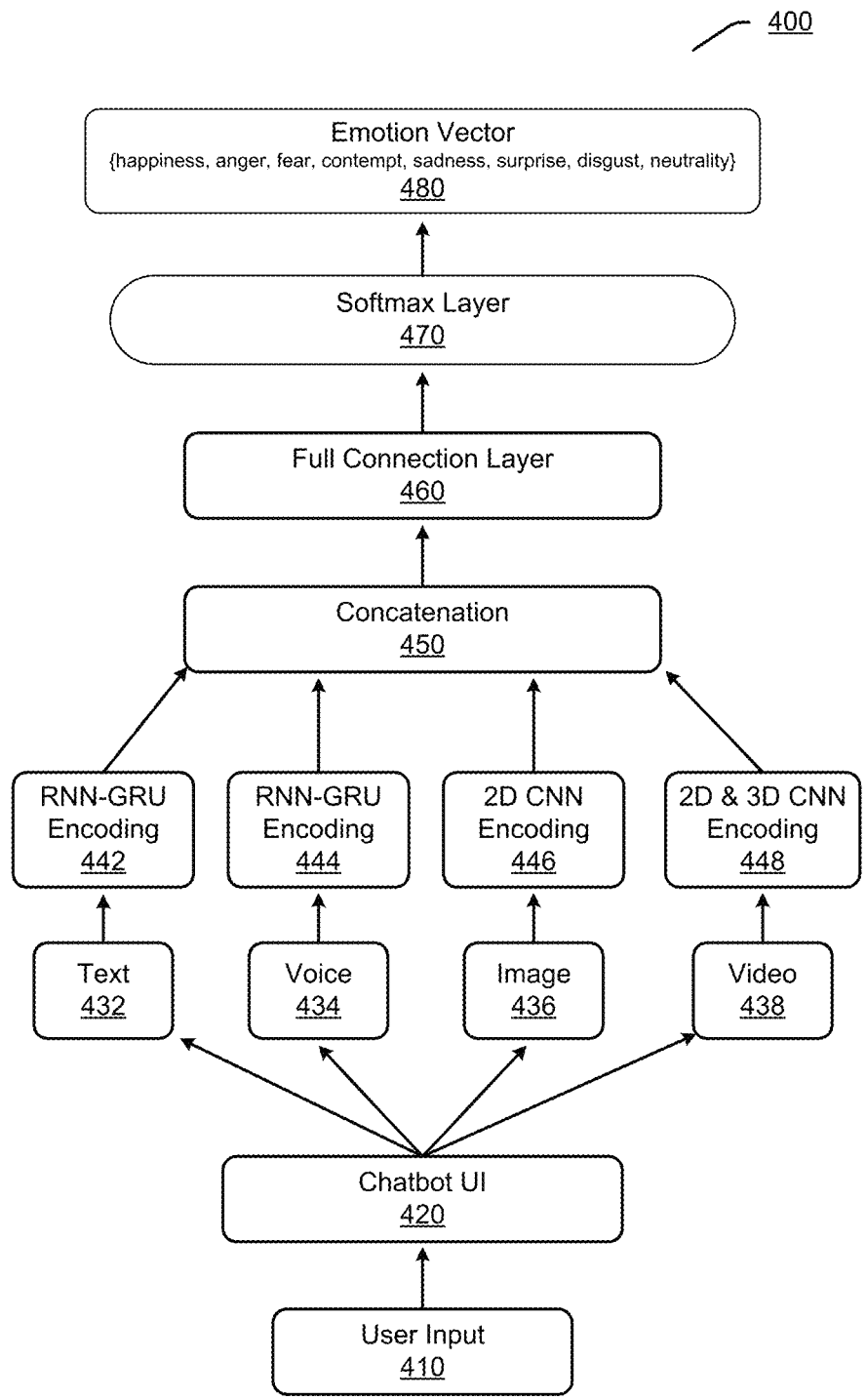
FIG. 4 illustrates an exemplary emotion analysis model according to an embodiment.

FIG. 4 illustrates an exemplary emotion analysis model 400 according to an embodiment. The emotion analysis model 400 may project an user input into dense vectors and further classify the user input into a corresponding emotion category in a vector space. The emotion analysis model 400 may be implemented by an emotion analysis classifier according to the embodiments of the present disclosure.

A user input 410 may be received through a UI 420 of a chatbot. The user input may be at least one of a text input 432, a voice input 434, an image input 436 and a video input 438. The text input 432 and the image input 436 may be captured in an input area of the UI 420, and the voice input 434 and the video input 438 may be captured by a microphone or a camera in a terminal device.

In an implementation, a recurrent neural network (RNN)-gated recurrent unit (GRU) encoding 442 may be performed on the text input 432. The RNN-GRU encoding 442 may be used for generating a dense vector representation for the text input 432. For example, the RNN-GRU encoding 442 may comprise a one-hot word embedding layer and one or more RNN-GRU layers. A Word2vec technique may be adopted for word embedding in the one-hot word embedding layer. The GRU in the RNN-GRU layers may be unidirectional, e.g., from left to right or from right to left, or may be bidirectional, e.g., both from left to right and from right to left.

Internal mechanism of the GRU may be defined by the following equations:

$$z_t = \sigma(W^{(z)}x_t + U^{(z)}h_{t-1} + b^{(z)}) \qquad \text{Equation (1)}$$

$$r_t = \sigma(W^{(r)}x_t + U^{(r)}h_{t-1} + b^{(r)}) \qquad \text{Equation (2)}$$

$$\tilde{h}_t = \tanh(Wx_t + r_t \circ Uh_{t-1} + b^{(h)}) \qquad \text{Equation (3)}$$

$$h_t = z_t \circ h_{t-1} + (1-z_t) \circ \tilde{h}_t \qquad \text{Equation (4)}$$

where ∘ is an element-wise product, $W^{(z)}$, $W^{(r)}$, W, $U^{(z)}$, $U^{(r)}$, U are weight matrixes, $W^{(z)}$, $W^{(r)}$, $W \in R^{n_H \times n_I}$, and $U^{(z)}$, $U^{(r)}$, $U \in R^{n_H \times n_H}$. Here, $n_H$ denotes a dimension of hidden layer, and $n_I$ denotes a dimension of input layer. The above equations may also be abbreviated as:

$$h_t = GRU(x_t, h_{t-1}) \qquad \text{Equation (5)}$$

Through the RNN-GRU encoding 442 as discussed above, a dense vector representation for the text input 432 may be obtained.

Figure 5:
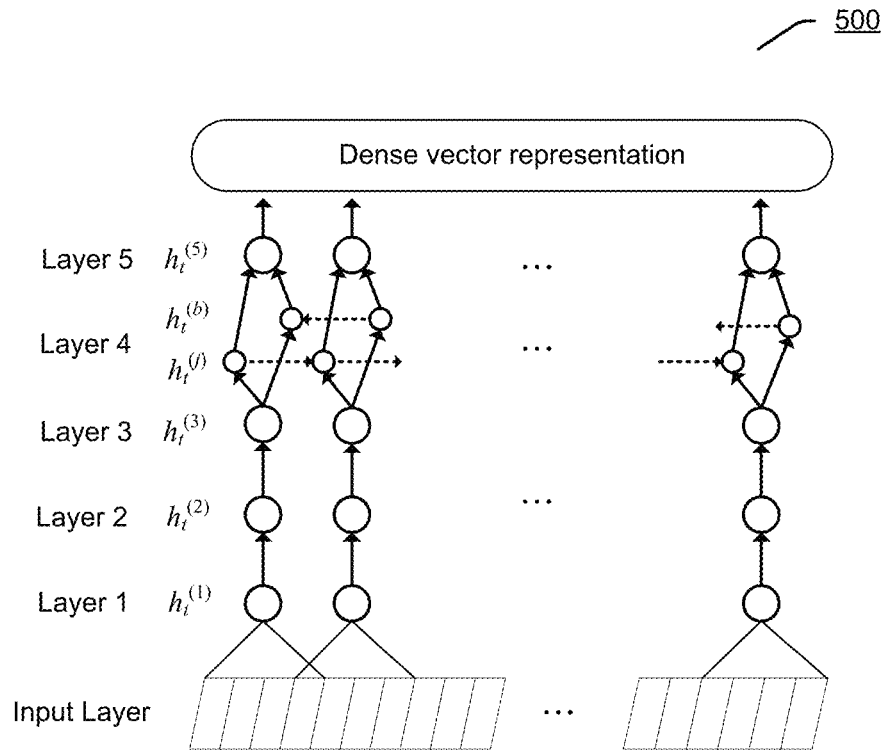
FIG. 5 illustrates an exemplary process for voice encoding according to an embodiment.

In an implementation, a RNN-GRU encoding 444 may be performed on the voice input 434. The RNN-GRU encoding 444 may be used for generating a dense vector representation for the voice input 434. FIG. 5 illustrates an exemplary process 500 for voice encoding according to an embodiment. The process 500 is an example of the RNN-GRU encoding 444. The process 500 may project an input voice segment x into a dense vector representation.

A voice segment $x^{(i)}$ may be inputted in an Input Layer. The voice segment $x^{(i)}$ may be a time-series with a length of $T^{(i)}$, and each slice is a vector of audio features, denoted as $x_t^{(i)}$, where t=1, 2, ..., $T^{(i)}$. Spectrograms may be used as input features.

As shown in FIG. 5, there are 5 layers of hidden units, denoted as Layer 1 to Layer 5. For an input sequence x, hidden units in Layer l are denoted as $h^{(l)}$, with a special case that $h^{(0)}$ may stand for the input sequence.

Layer 1, Layer 2 and Layer 3 are not recurrent layers. For Layer 1, at each time t, an output depends on a spectrogram frame $x_t$ along with a context of S frames on each side. Empirically, the value of S may be selected from {3, 5, 7, 9} that minimizes an error rate of a valuation set. Layer 2 and Layer 3 operate on independent data for each time step. Thus, for each time t, the first 3 layers may be computed as:

$$h_t^l = g(W^{(l)} h_t^{(l-1)} + b^{(l)})\qquad\text{Equation (6)}$$

In Equation (6), a clipped Rectified-Linear activation function g(z) is used, and $W^{(l)}$ and $b^{(l)}$ are weight matrix and bias parameter for Layer l respectively. The function g(z) may be denoted as $g(z) = \min\{\max\{\alpha, z\}, \beta\}$, where $\alpha$ and $\beta$ are hyper-parameters, and can be adjusted empirically.

Layer 4 is a bi-directional recurrent layer. This layer includes two sets of hidden units, one set for forward left-to-right recurrence $h^{(f)}$, and another set for backward right-to-left recurrence $h^{(b)}$. Internal mechanism of the GRU may follow the above Equations (1) to (5). Thus, $h^{(f)}$ and $h^{(b)}$ may be expressed by:

$$h_t^{(f)} = GRU(h_t^{(3)}, h_{t-1}^{(f)})\qquad\text{Equation (7)}$$

$$h_t^{(b)} = GRU(h_t^{(3)}, h_{t-1}^{(b)})\qquad\text{Equation (8)}$$

Layer 5 is a non-recurrent layer, which takes a concatenation of the forward units and the backward units in Layer 4 as inputs, and may be computed as:

$$h_t^5 = g(W^{(5)} h_t^{(4)} + b^{(5)})\qquad\text{Equation (9)}$$

where $h_t^{(4)}$ is the concatenation of $h_t^{(f)}$ and $h_t^{(b)}$.

Finally, a dense vector representation may be generated from outputs of Layer 5.

Through the RNN-GRU encoding 444 as discussed above, a dense vector representation for the voice input 434 may be obtained.

In an implementation, a 2D convolutional neutral network (CNN) encoding 446 may be performed on the image input 436. The 2D CNN encoding 446 may be used for generating a dense vector representation for the image input 436.

Figure 6:
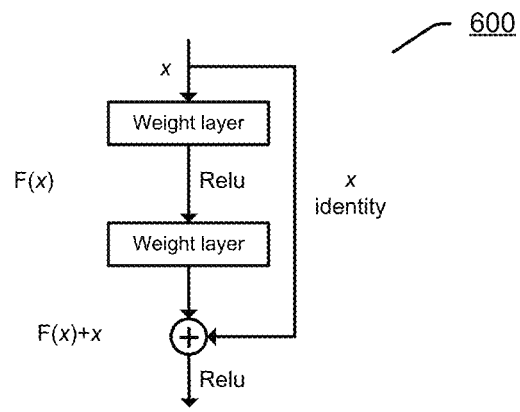
FIG. 6 illustrates an exemplary residual learning block for image encoding according to an embodiment.

Various techniques may be adopted in the 2D CNN encoding 446. For example, a residual network (ResNet) may be adopted in the 2D CNN encoding 446. The ResNet may comprise a plurality of residual learning blocks. FIG. 6 illustrates an exemplary residual learning block 600 for image encoding according to an embodiment. Formally, as for an input x, a desired underlying mapping may be denoted as H(x), and stacked nonlinear layers may fit another mapping of F(x):=H(x)−x. An original mapping may be recast into F(x)+x. It is hypothesized that it is easier to optimize residual mapping than to optimize original unreferenced mapping. To the extreme, if an identity mapping were optimal, it would be easier to push a residual to zero than to fit the identity mapping by a stack of nonlinear layers. The non-linear active function is a rectified linear unit (relu), which may be defined as: Relu(x)=max(0, x).

Figure 7:
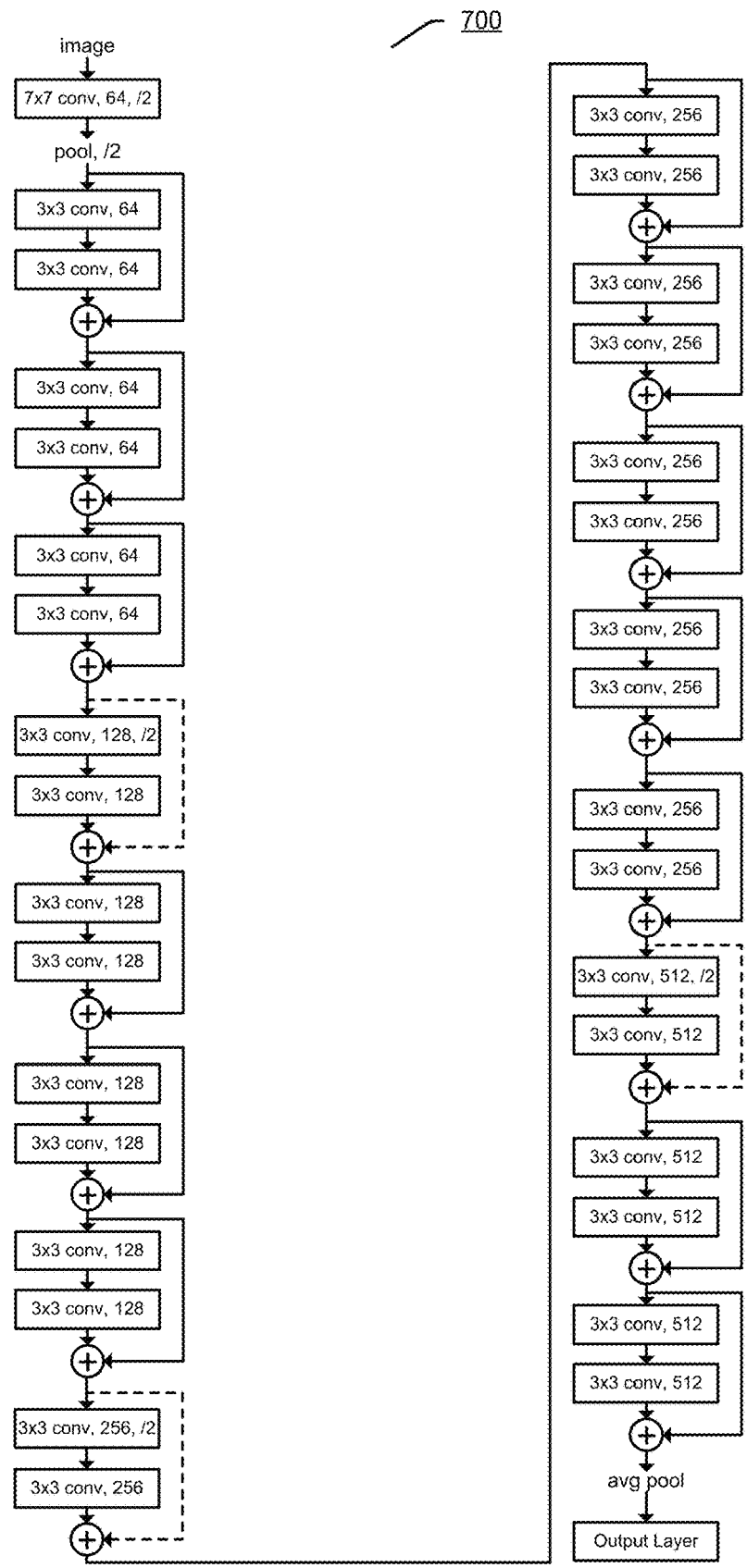
FIG. 7 illustrates an exemplary residual network for image encoding according to an embodiment.

Based on the residual learning block shown in FIG. 6, a residual network may be established. FIG. 7 illustrates an exemplary residual network 700 for image encoding according to an embodiment. The residual network 700 has 34 layers, which may provide a relative good accuracy and fast training/testing.

In FIG. 7, for example, "3*3 conv, 64" denotes that there are 64 filters, and each filter has a convolutional kernel or function and is in a scale of 3*3 pixels. "/2" denotes a double stride. "pool" denotes a pooling operation, and "avg pool" denotes an average pooling operation.

An output layer in FIG. 7 may output a dense vector representation for an image input based on, such as, a result of the average pooling operation.

It should be appreciated that the ResNet is an exemplary technique that can be adopted in the 2D CNN encoding 446, and any other techniques may be adopted in the 2D CNN encoding 446, such as, AlexNet, GoogLeNet, VGG-Net, etc.

Through the 2D CNN encoding 446 as discussed above, a dense vector representation for the image input 436 may be obtained.

In an implementation, a 2D and 3D CNN encoding 448 may be performed on the video input 438. The 2D and 3D CNN encoding 448 may be used for generating a dense vector representation for the video input 438.

Figure 8:
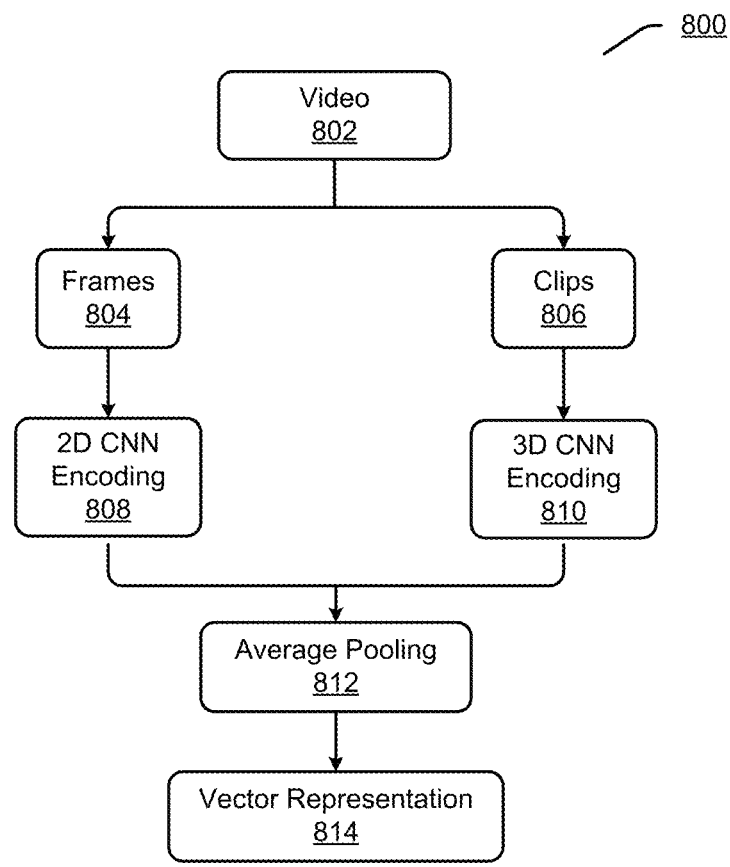
FIG. 8 illustrates an exemplary process for video encoding according to an embodiment.

FIG. 8 illustrates an exemplary process 800 for video encoding according to an embodiment. The process 800 may be based on both 2D CNN encoding and 3D CNN encoding.

As shown in FIG. 8, a video input 802 may be processed in terms of both frame and clip. As for frames 804 of the video input 802, a 2D CNN encoding 808 may be performed. The 2D CNN encoding 808 may adopt various techniques, e.g., ResNet, AlexNet, GoogLeNet, VGG-Net, etc. As for clips 806 of the video input 802, a 3D CNN encoding 810 may be performed. The 3D CNN encoding 810 may adopt various techniques, e.g., encoding by convolutional 3D filters, etc. An average pooling operation 812 may be performed on a combination of an output of the 2D CNN encoding 808 and an output of the 3D CNN encoding 810, so as to obtain a dense vector representation 814 for the video input 802.

It should be appreciated that the process 800 in FIG. 8 is an exemplary implementation of the 2D and 3D CNN encoding 448, and the 2D and 3D CNN encoding 448 is not limited to any details in the process 800.

Through the 2D and 3D CNN encoding 448 as discussed above, a dense vector representation for the video input 438 may be obtained.

According to the emotion analysis model 400 in FIG. 4, a concatenation operation 450 may be performed on outputs of the RNN-GRU encoding 442, the RNN-GRU encoding 444, the 2D CNN encoding 446, and the 2D and 3D CNN encoding 448. Through the concatenation operation 450, a concatenated vector may be obtained.

At a full connection layer 460, a full connection operation may be performed on the concatenated vector, e.g., multiplying the concatenated vector with a full connection matrix, such that a full connection vector which has a target dimension may be obtained.

A Softmax layer 470 may map the full connection vector to an emotion vector 480. The emotion vector 480 may have 8 dimensions, and each element in the emotion vector 480 is a probability of a corresponding emotion category. An emotion having the highest probability among the 8 categories of emotion may be selected as the emotion or major emotion of the user input 410.

The emotion analysis model 400 in FIG. 4 is a joint learning model which can project text, voice, image or video inputs into dense vectors and further classify the inputs into respective emotion categories in a vector space.

It should be appreciated that, although the emotion analysis model 400 is shown as being capable of processing four types of inputs, including text, voice, image and video inputs, the emotion analysis model 400 may also be configured for only processing one, two or three types of inputs.

For example, if only text information is available during training and testing, then the emotion analysis model 400 may be simplified as a simple "text emotion analysis model".

Through the emotion analysis model discussed above, a user's time sensitive emotions may be detected, and an emotion curve may be generated for the user, wherein the emotion curve may be formed from emotion states of the user within a time period. Herein, "emotion state" may also correspond to psychological condition.

Figure 9:
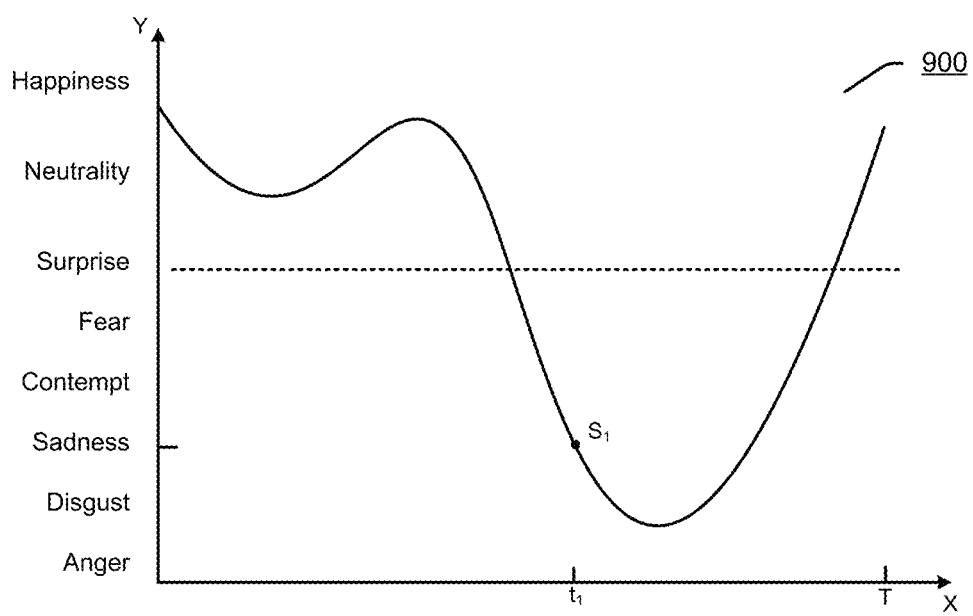
FIG. 9 illustrates an exemplary emotion curve according to an embodiment.

FIG. 9 illustrates an exemplary emotion curve 900 according to an embodiment. The emotion curve 900 may indicate emotion states of a user within a time period T. The time period T may be, such as, a week, two weeks, a month, etc. Although the emotion states are shown in a form of curve, it should be appreciated that the emotion curve 900 is actually formed by a plenty of discrete points, each point corresponding to an emotion determined at a moment.

The X axis in FIG. 9 is a time axis. The minimum time unit in the X axis may be customized, e.g., each message input by the user, each session including a plurality of messages, a certain number of sessions, etc.

The Y axis in FIG. 9 is an emotion state axis. In an implementation, an emotion at each scale in the Y axis and distributions of the scales in the Y axis may be determined through, such as, a Principal Component Analysis (PCA) technique.

Taking a point $S_1$ in the emotion curve 900 as an example, the point $S_1$ may indicate that the user's emotion is "sadness" at the time $t_1$. The emotion of the point $S_1$ may be determined based on, such as, a message input by the user at the time $t_1$, a session ends at the time $t_1$, a group of sessions ends at the time $t_1$, etc. The emotion analysis model may be used for determining the emotion "sadness" of the point $S_1$ based on the message input by the user, the session, the group of sessions, etc.

The dotted line in FIG. 9 is drawn empirically, which may be used for discriminating negative emotions. For example, the part of the emotion curve 900 that is below the dotted line may be deemed as corresponding to negative emotions. The negative emotions may comprise, such as, anger, disgust, sadness, contempt, fear, or even surprise.

Figure 10:
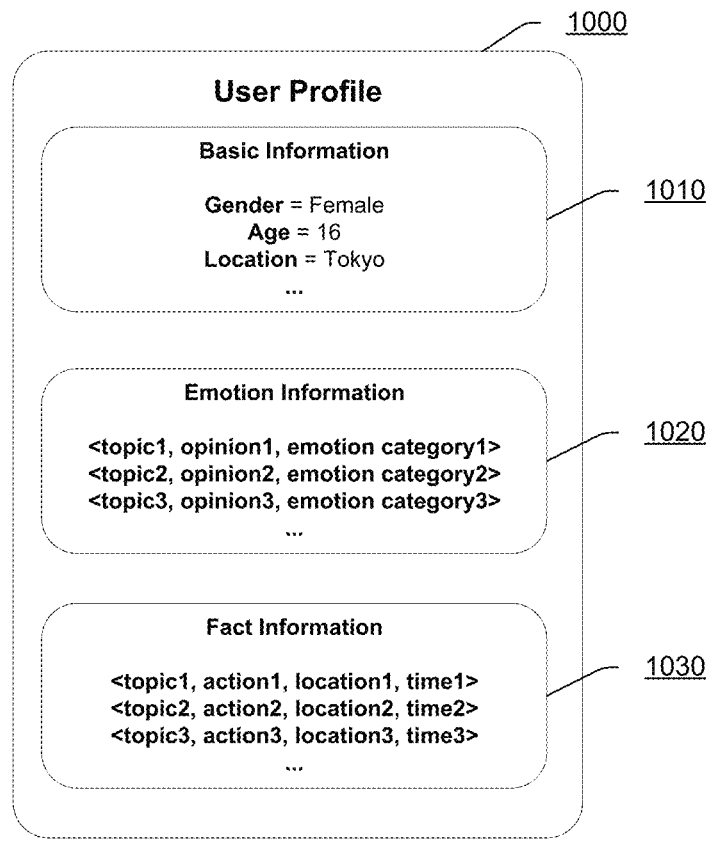
FIG. 10 illustrates an exemplary user profile according to an embodiment.

FIG. 10 illustrates an exemplary user profile 1000 according to an embodiment. The user profile 1000 may comprise at least one of basic information 1010, emotion information 1020 and fact information 1030.

The basic information 1010 may comprise biography of the user, e.g., gender, age, location, etc. Various models may be used for predicting gender, age, location information in the basic information 1010 from session logs of the user, especially from historical queries of the user.

For a gender classification model, the input is <user id, queries> and the output is tags of "male" or "female". A number of clues in the queries can be utilized, such as, "my wife does not do any family works" is likely spoken by a married man, "my husband is quite busy recently" is more frequently spoken by a married woman, etc.

For an age predication model, the input is <user id, queries> and the output is a tag of, e.g., "10+", "20+", "30+", "40+", "50+" or "60+", where "10+" indicates an age between 10 and 20, "20+" indicates an age between 20 and 30, "30+" indicates an age between 30 and 40, and so on. The age prediction model may determine age information based on the queries. For example, if a user says "I am a senior middle school student" in a session, it may be determined that the age of the user is "10+". If a user says "I am already retired" in a session, it may be determined that the user is very likely to be "60+".

For a location detection model, the input is <user id, queries> and the output may be at least one tag of location. The location detection model may determine location information based on the queries. For example, if a user says "Do you have any suggestions on restaurants for working lunch around Ueno?" in a session, it may be determined that the user is working around Ueno in Tokyo.

The above three classification or detection models may be trained based on training data of <user id, queries, target tags>. Training data may be manually created. The features for the training may comprise:

Target product category or company of the query: for example, females may have stronger tendency to domains of cosmetics and their related companies.

Disease keywords included in the user's historical query: for example, man and woman may have shared diseases and gender-sensitive diseases, such as mammary-related diseases for woman and prostate-related diseases for man.

The list of location related words that the user mentioned the most: an existing location lexicon may be used for detecting location related words in the user's queries.

Word ngrams: unigrams and bigrams for words in the query.

Character ngrams: for each word in the query, character ngrams are extracted. For example, 4-grams and 5-grams are used in this model.

Word skip-grams: for all the trigrams and 4-grams in the query, one of the words is replaced by a symbol, such as, "*", to indicate the presence of non-contiguous words.

Brown cluster ngrams: Brown clusters are used for representing words in query, and then unigrams and bigrams are extracted as features.

Part-of-speech (POS) tags: the presence or absence of POS tags is used as binary features.

Social network related words: number of hashtags, emoticons, elongated words, and punctuations in the query are used as features.

Word2vec cluster ngrams: the word2vec tool (Mikolov et al., 2013) may be used for learning 100-dimensional word embedding from a social network dataset. Then, K-means algorithm and L2 distance of word vectors may be employed to cluster the million-level vocabulary into, such as, 200 classes. The classes are used for representing generalized words in the query.

A multiple-class support vector machine (SVM) model may be trained using the above exemplary features. These three models may share similar feature templates.

It should be appreciated that the basic information 1010 is not limited to comprise gender, age and location, but may comprise any further information about the user, e.g., profession, religious belief, preferences, etc.

The emotion information 1020 may reflect the user's emotions on certain topics. The emotion information 1020 may comprise a plurality of emotion information items. Each emotion information item may comprise at least one of: a topic of interest involved in the session logs of the user, the user's opinion on the topic, emotion category of the opinion, etc. An emotion information item may be in a form of <topic, opinion, emotion category>. For example, as for a message "What a wonderful day! I'm so glad to organize the home party!" from the user, a topic "home party" and an opinion "glad to organize" may be extracted from the message, and through performing emotion analysis on the message, an emotion category "happiness" may be derived. Thus, an emotion information item <home party, glad to organize, happiness> may be obtained from the message. It should be appreciated that the emotion information 1020 is not limited to the form of <topic, opinion, emotion category>, and may also be in any other forms, e.g., <topic, emotion category>, etc.

The fact information 1030 may reflect various facts talked by the user. The fact information 1030 may comprise a plurality of fact information items. Each fact information item may comprise at least one of: a topic, action of the user, location, time, etc. A fact information item may be in a form of <topic, action, location, time>. For example, as for a session log "User: Do you like Chihuahua? Chatbot: Yes, how about you? User: Me too! I have one in my home. I brought it back to home two years ago." between the user and the chatbot, a topic "Chihuahua", an action "brought back", a location "home" and time "2015" may be extracted from the session log, wherein the time "2015" is derived based on the expression "two years ago" and the current year "2017". Thus, a fact information item <Chihuahua, brought back, home, 2015> may be obtained from the session log. It should be appreciated that the fact information 1030 is not limited to the form of <topic, action, location, time>, and may also be in any other forms, e.g., <topic, action, location>, <topic, action, time>, <topic, location, time>, etc. In an implementation, the fact information may be mined directly from messages of the users. In an implementation, the chatbot may also initiatively ask the user's opinion on a topic so as to complete a fact information item, such as, the question "how about you?" in the above session log is provided by the chatbot for obtaining the user's opinion on "Chihuahua".

Figure 11:
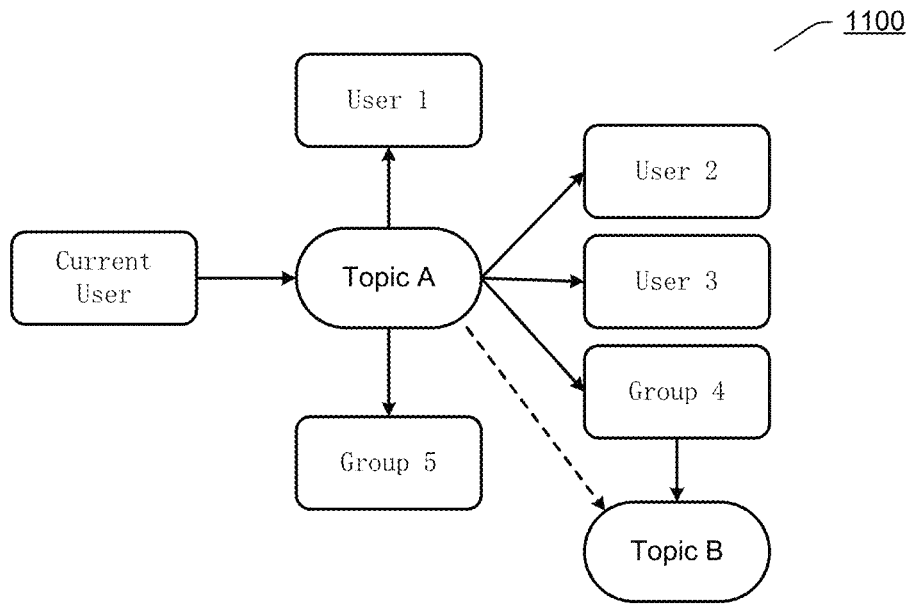
FIG. 11 illustrates an exemplary user-topic transferring model according to an embodiment.

It can be seen that the user profile 1000 may comprise topics interested or talked by the user. The topics in the user profile 1000 may also be extended. FIG. 11 illustrates an exemplary user-topic transferring model 1100 according to an embodiment. The user-topic transferring model 1100 may be used for user-topic detection and topic-topic connection, and accordingly extending topics in a user profile.

In the case of user-topic detection, the model 1100 may be applied in two scenarios, one is for individual users, and another is for group users.

As for the scenario of individual users: under this scenario, when a "Topic A" of the current user, such as one "event", is collected and added in the user profile, there is a "transfer" action that starts from the "node" of the current user to other users through the "Topic A". There may be an active signal sent from "Topic A" to other users, such as Users 1-3 and Groups 4-5. The target of this "transfer" action is to activate other users again in case that these users are not "active" to "Topic A" in a relatively long time. Consequent actions may be performed. One consequent action may comprise: proactively selecting a part of the users, such as Users 1-3 and Groups 4-5, and asking questions about whether they still have an opinion to "Topic A". Another consequent action may comprise: performing deep propagation from the selected users to their topics other than "Topic A", such as "Topic B". When "Topic A" and "Topic B" are linked by more and more users, then a similarity score between "Topic A" and "Topic B" may be updated to be higher. For example, assuming that "Topic A" is "Chihuahua" and "Topic B" is "Pomeranian", if more and more users share these two topics, then their "similarity" may be increased with a linear relevance with the number of users.

As for the scenario of group users: the model 1100 may detect topics that are introduced by or involved with one user and keep track of other users' opinions/comments to these topics. Also, time point/period and location information may also be detected based on context information.

Based on the above discussion, one type of output of the model 1100 may be tuples of <user, topic>.

In the case of topic-topic connection, the model 1100 may score relationship between every two topics, such as "Topic A" and "Topic B". Accordingly, another type of output of the model 1100 may be tuples of <topic1, topic2> or <topic1, topic2, relationship score>. Since each topic is associated with a number of users, through linking two topics, two groups of users may be further implicitly connected.

Through the model 1100, topics in the user profile may be continuously extended and updated.

Figure 12:
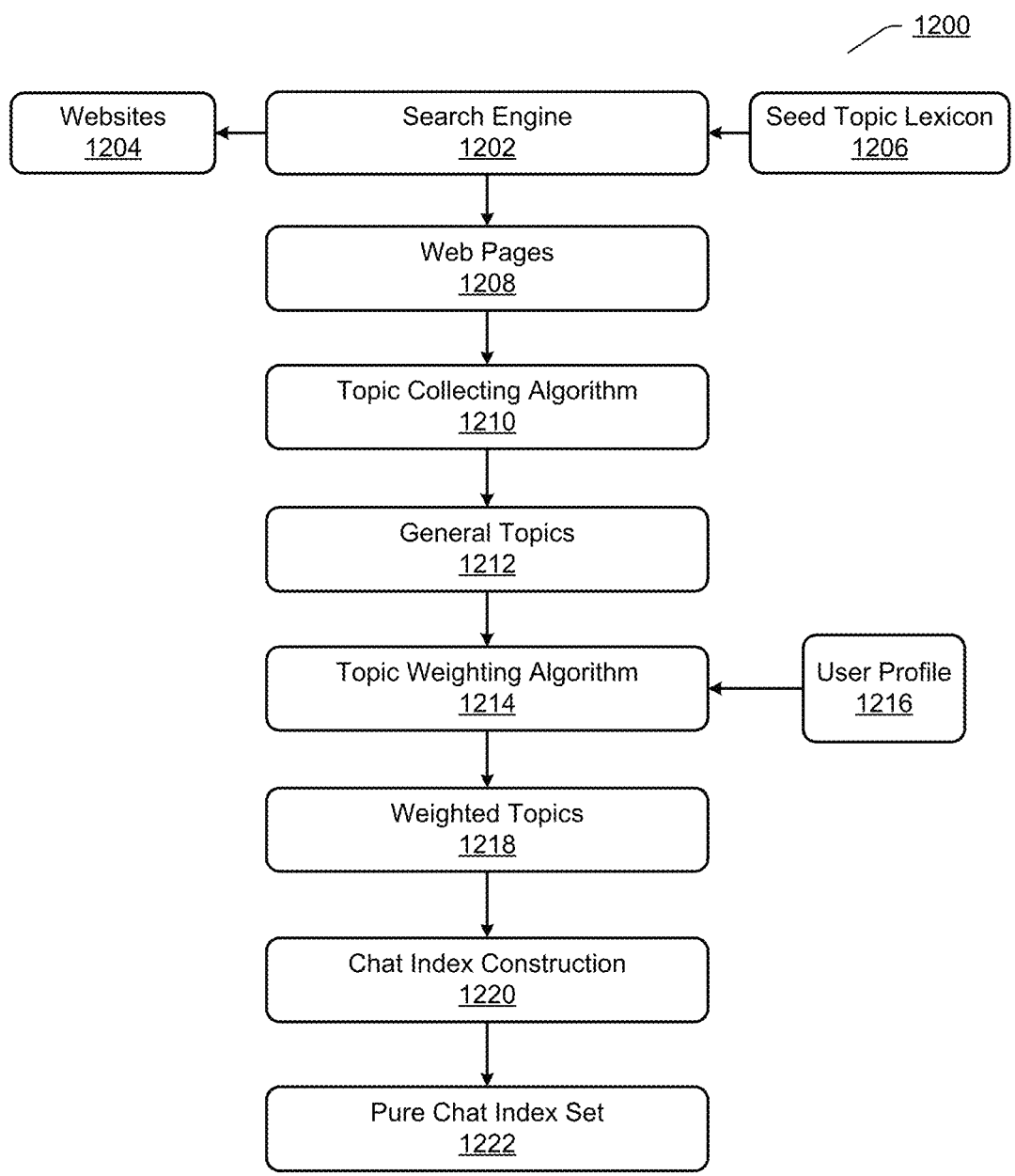
FIG. 12 illustrates an exemplary process for establishing a pure chat index set according to an embodiment.

FIG. 12 illustrates an exemplary process 1200 for establishing a pure chat index set according to an embodiment. The process 1200 may be implemented for establishing the target user oriented pure chat index set based at least on topics interested by a user, and thus the established pure chat index set may be used for providing responses in a session in consideration of the topics interested by the user.

According to the process 1200, a search engine 1202 may be used for accessing websites 1204 on the network, and utilizes a seed topic lexicon 1206 to crawl web pages 1208, wherein the seed topic lexicon 1206 comprises a list of predetermined seed topics and the web pages 1208 contain at least one seed topic. Depending on various types of the websites 1204, the web pages 1208 may be in a form of plain text or in a form of QA pair.

In an implementation, before performing subsequent operations, a pre-process may be alternatively performed on the web pages 1208 so as to resolve ambiguity caused by pronouns and abbreviations in the web pages 1208. Various existing techniques may be adopted in the pre-process, such as, Named Entity Recognition (NER), coreference resolution of pronouns and normal nouns, unification of abbreviations, unification and automatic computing of time expressions, etc. Taking the coreference resolution as an example, a machine learning model may be used for computing probabilities of candidate named entities that correspond to a given pronoun or normal noun in a web page, and accordingly ambiguity caused by the given pronoun or normal noun may be removed by replacing the given pronoun or normal noun by a top-ranked candidate named entity.

At 1210, the web pages 1208 or the pro-processed web pages 1208 may be input to a topic collecting algorithm. The topic collecting algorithm may be used for collecting general topics 1212 from the web pages 1208. In an implementation, named entities, location related phrases, time related phrases, etc. in the web pages 1208 may be extracted as the general topics 1212.

At 1214, a topic weighting algorithm may be applied on the general topics 1212 so as to weight the general topics 1212 based on a user profile 1216 of the user and obtain weighted topics 1218. The user profile 1216 may comprise a plurality of topics that are interested or talked by the user, and through giving higher weights for those topics most frequently talked by the user, the topic weighting algorithm may facilitate to find the user's "personalized" topics from the general topics 1212. The personalization may grow as session logs between the user and the chatbot are increasing, since the user profile may better capture the user's interests and emotional opinions on more and more topics.

At 1220, a chat index construction may be performed based on the weighted topics 1218 so as to form a pure chat index set 1222. In an implementation, the chat index construction may generate QA pairs from web pages associated with the weighted topics 1218. In the case that the web pages are in a form of plain text, various existing techniques may be adopted in the chat index construction. For example, a dependency tree based QA pair constructing technique may be adopted, wherein for a sentence in plain texts in a web page, predicates and/or arguments may form answers and the remaining part of the sentence may form questions. Moreover, for example, for a list of sentences in the plain texts, one or more former sentences may form a question, and the consequent sentences may form an answer. In the case that the web pages are in a form of QA pair, the QA pairs in the web pages may be extracted directly by the chat index construction. It should be appreciated that the above chat index construction may be performed based on all of the weighted topics 1218, or a part of the weighted topics 1218, e.g., one or more top-ranked weighted topics.

The QA pairs generated or extracted by the chat index construction may be added into the pure chat index set 1222. Since the pure chat index set 1222 is established based at least on the user profile 1216, it may be used for providing responses in consideration of topics interested by the user.

Figure 13:
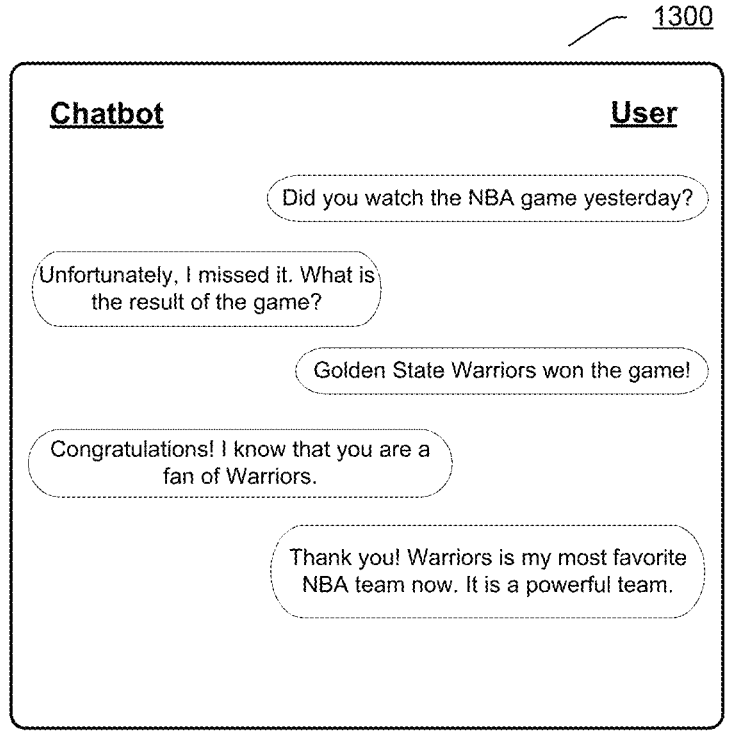
FIG. 13 illustrates an exemplary chat window according to an embodiment.

FIG. 13 illustrates an exemplary chat window 1300 according to an embodiment. The chat window 1300 shows a chat flow in which the chatbot may provide responses based on a pure chat index set as established through the process 1200.

The user may ask the chatbot "Did you watch the NBA game yesterday?". The chatbot may respond by "Unfortunately, I missed it. What is the result of the game?". When receiving a message "Golden State Warriors won the game!" from the user, the chatbot may match the "Golden State Warriors" in the message with index items in the pure chat index. Assuming that the chatbot has previously detected that Golden State Warriors is a topic interested by the user, e.g., the user is a fan of Golden State Warriors, and one or more corresponding index items have been included in the pure chat index, the chatbot may return a response "Congratulations! I know that you are a fan of Warriors" which is generated based at least on the index items associated with this topic interested by the user.

Figure 14:
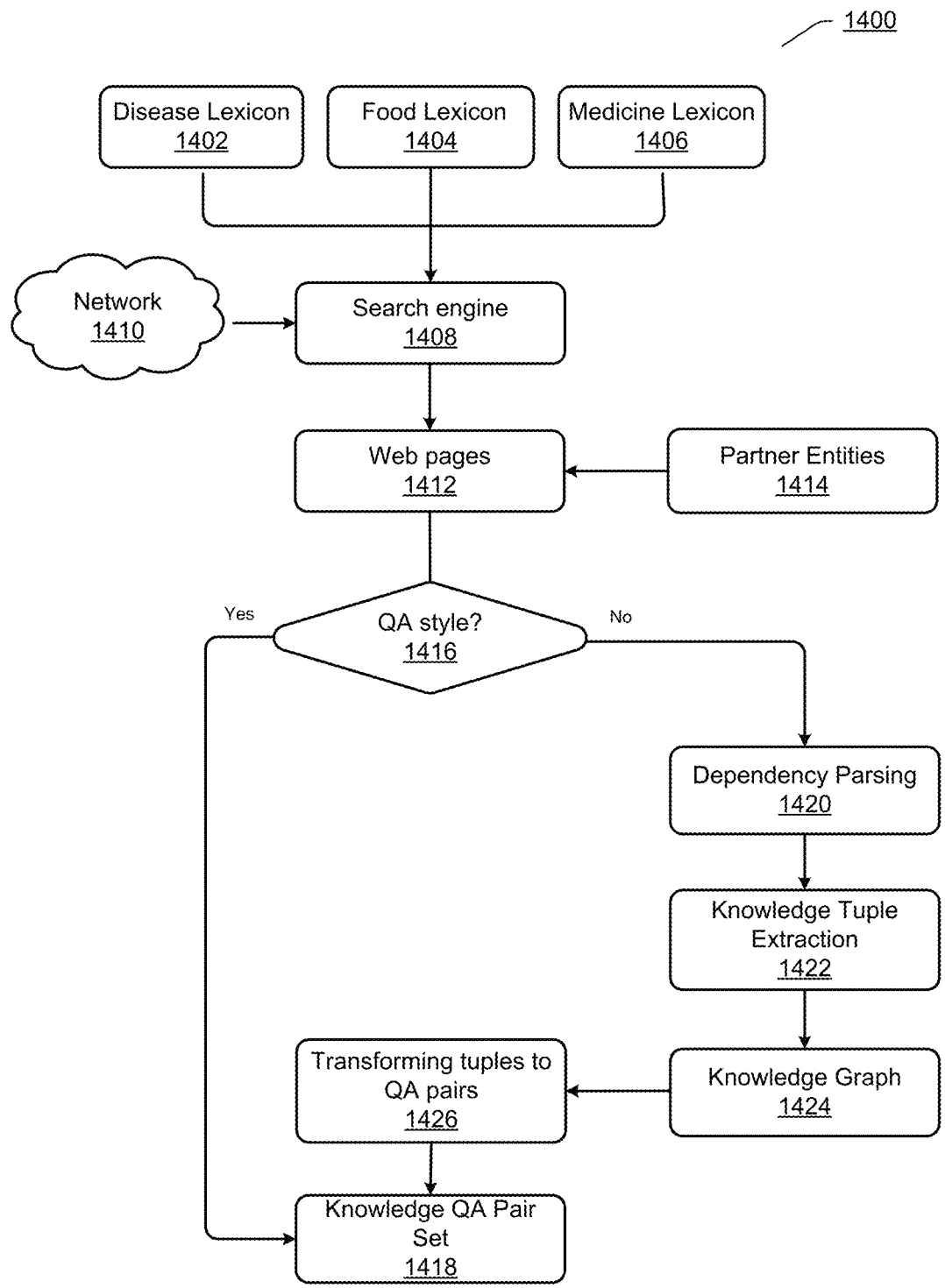
FIG. 14 illustrates an exemplary process for establishing a knowledge graph and a knowledge question-answer (QA) pair set according to an embodiment.

FIG. 14 illustrates an exemplary process 1400 for establishing a knowledge graph and a knowledge QA pair set according to an embodiment.

At least one of a disease lexicon 1402, a food lexicon 1404 and a medicine lexicon 1406 may be used for providing searching keywords for a search engine 1408. The disease lexicon 1402 comprises names of various diseases. The food lexicon 1404 comprises names of various foods or dishes. The medicine lexicon 1406 comprises names of various medicines. It should be appreciated that any other types of lexicon may be used for providing searching keywords.

Each entry in the disease lexicon 1402, the food lexicon 1404 and the medicine lexicon 1406 may be provided to the search engine 1408. The search engine 1408 may crawl relevant web pages 1412 from the network 1410 by using the entry as a searching keyword. Additionally or alternatively, the web pages 1412 may also be provided by partner entities 1414. The partner entities 1414 may be, such as, producers, sellers, etc. that can supply the web pages 1412 or related data. The web pages 1412 may contain at least one type of disease, at least one type of food, at least one type of medicine, etc., and thus the web pages 1412 may be construed as including knowledge about diseases, foods and/or medicines.

At 1416, it may be determined whether a web page is in a QA pair style. If yes, QA pairs in the web page may be added into a knowledge QA pair set 1418. If not, that is, the web page is in a form of plain text, dependency parsing may be performed on the plain text at 1420. Syntactic structures of sentences in the plain text may be identified through dependency parsing at 1420, and then knowledge tuples may be extracted from dependency trees of the sentences at 1422. The knowledge tuples may further form a knowledge graph 1424.

Figure 15A:
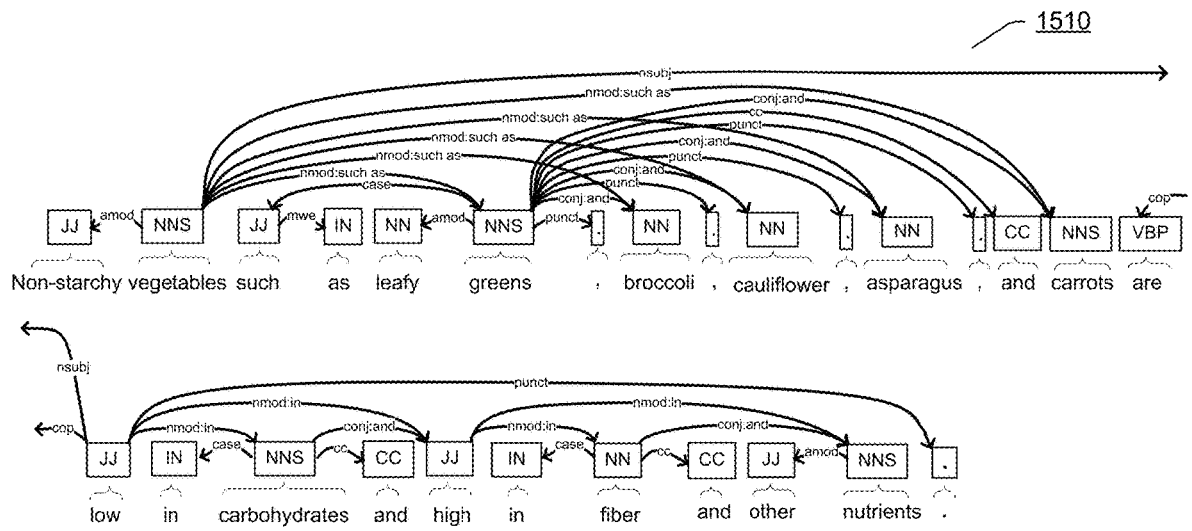
FIG. 15A-FIG. 15D illustrate exemplary dependency parsing according to an embodiment.
Figure 15B:
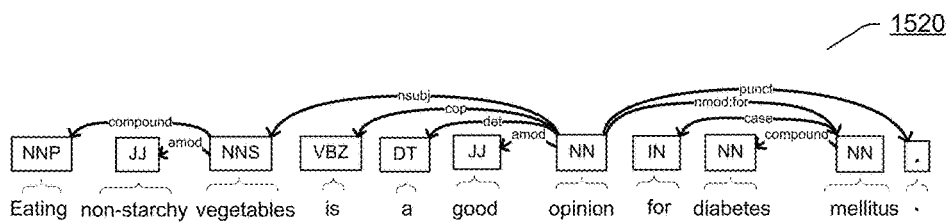

FIG. 15A and FIG. 15B illustrate exemplary dependency parsing 1510 and 1520 according to an embodiment. Dependency trees are obtained through performing the dependency parsing 1510 and 1520 on two sentences. It should be appreciated that various dependency parsing techniques may be used here for performing the dependency parsing.

Knowledge tuples may be extracted from the dependency trees of the sentences. The extracting process may follow dependency arcs which link predicates with arguments and link entities with syntactic relations.

It is assumed that the food lexicon 1404 contains entities "non-starchy vegetables", "leafy greens", "broccoli", "cauliflower", "asparagus" and "carrots", and the disease lexicon 1402 contains an entity "diabetes mellitus". Then, the "non-starchy vegetables" and a disease "diabetes mellitus" may be linked by the following dependency arcs shown in FIG. 15A and FIG. 15B: <non-starchy vegetables, good opinion, nsubj> where "nsubj" denotes noun-style subject of the dependency arc; and <good opinion, diabetes mellitus, nmod:for> where "nmod:for" denotes a noun-style modification relation guided by keyword "for" between "good opinion" and "diabetes mellitus". Then, the following tuple may be obtained by combining these two dependency arcs together: <non-starchy vegetables, diabetes mellitus, good opinion>.

The above is an exemplary tuple in a form of <entity, entity, relation>, such as, <food, disease, relation>. Through this way, various available relationships for foods and diseases that appear in the plain text may be collected.

Moreover, relations of entities that are both foods or both diseases may also be extracted. Taking food entities as an example, the following dependency arcs are shown in FIG. 15A: <non-starchy vegetables, leafy greens, nmod:such_as>where "nmod" denotes a noun-style modification relation guided by key phrase "such as"; and <leafy greens, broccoli, conj:and>where "conj" is for conjunction and guided by keyword "and". If the "nmod:such_as" dependency type is mapped into "is_a" relation which is more generalized, then the following tuples of "is_a" relation may be obtained: <leafy greens, non-starchy vegetables, is a> which implies that "leafy greens is a non-starchy vegetable"; and <broccoli, non-starchy vegetables, is a> which implies that "broccoli is a non-starchy vegetable". Through this way, available relationships for foods that appear in the plain text may be collected. Similarly, available relationships for diseases that appear in the plain text may also be collected.

It should be appreciated that although the above discussion about FIG. 15A and FIG. 15B only involves the "disease" domain and the "food" domain, similar processes may also be extended to the "medicine" domain, and thus the extracted tuples may also be in a form of <disease, food, medicine, relation>, <disease, medicine, relation>, <food, medicine, relation>, etc.

The extracted tuples may be used for forming or updating the knowledge graph 1424. The knowledge graph 1424 may be a disease domain knowledge graph which includes knowledge information related to various diseases, a food domain knowledge graph which includes knowledge information related to various foods, a medicine domain knowledge graph which includes knowledge information related to various medicines, or a knowledge graph that is related to any combinations of diseases, foods and medicines.

In an implementation, a knowledge graph that is related to diseases, foods and medicines may be obtained through linking a disease domain knowledge graph, a food domain knowledge graph and a medicine domain knowledge graph. The linking may be based on at least one of the following heuristic rules:

Link by the knowledge tuples mined using all of the three lexicons.

Link by co-occurrence frequencies of one disease, one food and one medicine that appear in one sentence, one paragraph, or even one document. Different similarity scores may be assigned based on these co-occurrences so that diseases, foods and medicines can be linked making use of these similarity scores.

Link by latent semantic similarity scores. A joint word2vec model may be trained using disease domain, food domain and medicine domain web pages, and then may be used for computing "latent semantic scores" of a pair of <disease, food>, <disease, medicine>, and <food, medicine> by dot-product of their vector representations.

In FIG. 14, the tuples in the knowledge graph 1424 may be transformed to QA pairs at 1426. Taking a tuple <diabetes mellitus, pumpkin, suitable food> as an example, this tuple describes the relation "suitable food" between an entity "diabetes mellitus", which is a disease name, and an entity "pumpkin", which is a food name. This tuple may be transformed to the following question-answer pairs:

Question=What is the suitable food for diabetes mellitus? Answer=Pumpkin.

Question=Is pumpkin suitable food for diabetes mellitus? Answer=Yes, it is.

Question=What kind of disease is pumpkin a suitable food? Answer=Diabetes mellitus.

In this way, one tuple may be automatically transformed into a plurality of QA pairs in natural language. These natural language style QA pairs may be used for providing natural language style responses to the user. The QA pairs transformed from knowledge tuples may be added into the knowledge QA pair set 1418.

A learning-to-rank (LTR) model may be used for ranking candidate answers in the knowledge QA pair set 1418 by given a query of the user. In some implementations, latent semantic features may be adopted for comparing a query and a candidate <question, answer> pair in a dense vector space.

In an implementation, "dependency arc matching" score may be adopted in the LTR model. Dependency parsing may be performed on both the query and a question or answer in each candidate <question, answer> pair, and then dependency arcs of the query and the question or answer may be compared to obtain a similarity score.

Figure 15C:
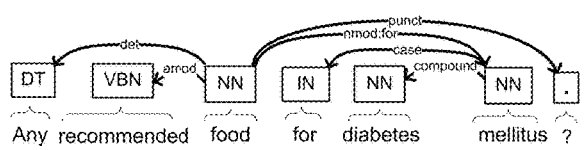
Figure 15D:
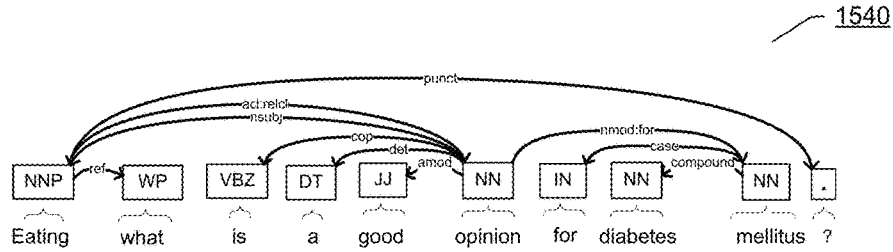

Given a query "Any recommended food for diabetes mellitus?", FIG. 15C illustrates an exemplary dependency parsing 1530 on this query according to an embodiment. Moreover, given a candidate question "Eating what is a good opinion for diabetes mellitus?" in a candidate <question, answer> pair, FIG. 15D illustrates an exemplary dependency parsing 1540 on this candidate question according to an embodiment.

The query and the candidate question share the same dependency arcs, such as, "diabetes-compound-mellitus", "for-case-mellitus", etc., which are explicit word and arc matching. Moreover, similar dependency arcs are also shared between the query and the candidate question, which are implicit dense vector space matching, such as, "food-nmod: for-mellitus" in the query is similar with "opinion-nmod: for-mellitus" in the candidate question, "recommended-amod-food" in the query is similar with "good-amod-opinion" in the candidate question, etc. The comparison of dependency arcs may be performed in latent vector spaces, through projecting the dependency arcs into dense space vectors and then computing similarity scores of the two vectors by, such as, cosine function.

In an implementation, the LTR model may employ a gradient boosting decision tree (GBDT) algorithm for ranking candidate QA pairs for a query, and the following features may be utilized in the GBDT algorithm.

Implicit/explicit dependency arc similarity score between the dependency trees of the query and the candidate question. The explicit dependency arc similarity score is obtained based on text string level comparison of the dependency arcs. The implicit dependency arc similarity score is obtained based on dense space vector level comparison of the dependency arcs.

Implicit/explicit dependency arc similarity score between the dependency trees of the query and the candidate answer.

Frequency of the user's and other users' positive feedbacks for the candidate answer.

Language model for information retrieval with respect to the query q and the candidate question Q: Given a query q and a candidate question Q, this feature measures the relevance between q and Q through:

$$P(q|Q) = \Pi_{w \in q}[(1-\lambda)P_{ml}(w|Q) + \lambda P_{ml}(w|C)] \quad \text{Equation (10)}$$

where $P_{ml}(w|Q)$ is the maximum likelihood of word w estimated from Q, and $P_{ml}(w|C)$ is a smoothing item that is computed as the maximum likelihood estimation in a large-scale corpus C. Here the corpus C may be the knowledge QA pair set. The smoothing item avoids zero probability, which stems from those words appearing in the candidate question Q but not in the query q. The $\lambda$ is a parameter that acts as a trade-off between the likelihood and the smoothing item, where $\lambda \in (0, 1)$. This feature works well when there are a number of words overlapped between the query and the candidate question.

Language model for information retrieval with respect to the query q and the candidate answer A. In this language model, similarity score between the query and a candidate answer is also computed using Equation (10) by taking the candidate answer A instead of Q in Equation (10).

Translation-based language models with respect to the query q and the candidate question Q. This feature learns word-to-word and/or phrase-to-phrase translation probability from, such as, question-answer pairs, and incorporates the learned information into maximum likelihood.

Given the query q and the candidate question Q, a translation-based language model is defined as:

$$P_{trb}(q|Q) = \Pi w \in q[(1-\lambda)P_{mx}(w|Q) + \lambda P_{ml}(w|c)] \quad \text{Equation (11)}$$

$$P_{mx}(w|Q) = \alpha P_{ml}(w|Q) + \beta P_{tr}(w|Q) \quad \text{Equation (12)}$$

$$P_{tr}(w|Q) = \Sigma_{v \in Q} P_{tp}(w|v) P_{ml}(v|Q) \quad \text{Equation (13)}$$

Here $\lambda$, $\alpha$ and $\beta$ are parameters satisfying $\lambda \in (0, 1)$ and $\alpha + \beta = 1$. $P_{tp}(w|v)$ is a translation probability from word v in Q to word w in q.

Translation-based language models with respect to the query q and the candidate answer A. In this language model, similarity score between the query and the candidate answer is also computed using Equations (11)-(13) by taking the candidate answer A instead of the Q in Equations (11)-(13).

Edit distance between the query and the candidate question in a word or character level.

Maximum subsequence ratio between the query and the candidate question.

Recurrent neural network (RNN) by using gated recurrent units (GRUs) as encoding. The encoding projects a sequence of words, a sequence of phrases, or a sequence of dependency arcs into a dense vector space, which is a latent semantic representation of the sequence. The query and the candidate question or answer may be provided to a RNN-GRU layer respectively to obtain corresponding dense vectors, and then similar score between the two dense vectors may be computed.

It should be appreciated that all the above features in the GBDT algorithm are exemplary, and more or less features may be adopted in the GBDT algorithm in various implementations.

Figure 16:
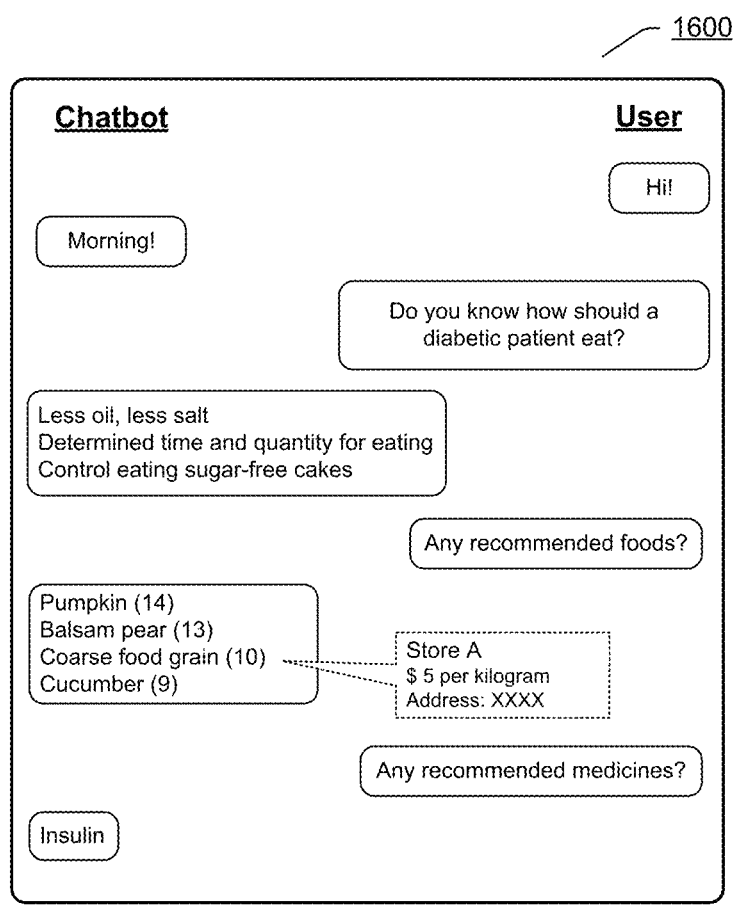
FIG. 16 illustrates an exemplary chat window according to an embodiment.

The knowledge graph 1424 and further the knowledge QA pair set 1418 may be used for providing knowledge about diseases, foods and/or medicines in a response to a message from the user. FIG. 16 illustrates an exemplary chat window 1600 according to an embodiment. The chat window 1600 shows a chat flow in which the chatbot may provide responses based on a knowledge graph and/or a knowledge QA pair set as established through the process 1400.

When receiving a message "Do you know how should a diabetic patient eat?" in a session, the chatbot may determine that the user is requiring diet knowledge about the disease "diabetes mellitus". The chatbot may extract disease knowledge and food knowledge related to "diabetes mellitus" from the knowledge graph and/or the knowledge QA pair set, and accordingly provide a response, e.g., "Less oil, less salt", "Determined time and quantity for eating", "Control eating sugar-free cakes", etc.

When the user further inputs a message "Any recommended foods?", the chatbot may further extract detailed food knowledge related to "diabetes mellitus" from the knowledge graph and/or the knowledge QA pair set, such as, names of foods that are suitable for a diabetic patient. For example, the chatbot may provide a response including "Pumpkin (14)", "Balsam pear (13)", "Coarse food grain (10)", "Cucumber (9)", etc., wherein the numbers following food names indicate frequencies of the corresponding foods being given positive feedbacks by all the users. The response may also include links to product selling information. For example, if the user clicks on or moves the cursor onto "Coarse food grain (10)", corresponding selling information may be displayed, such as, "Store A", "$5 per kilogram", "Address: xxxx", etc.

When the user further inputs a message "Any recommended medicines?", the chatbot may extract medicine knowledge related to "diabetes mellitus" from the knowledge graph and/or the knowledge QA pair set. For example, the chatbot may provide a response including a medicine name "Insulin" which is suitable for a diabetic patient.

According to the embodiments of the present invention, the chatbot may create memory records based on session logs between the chatbot and the user. A memory record may be created based at least on a group of images and a group of corresponding textual descriptions.

Figure 17:
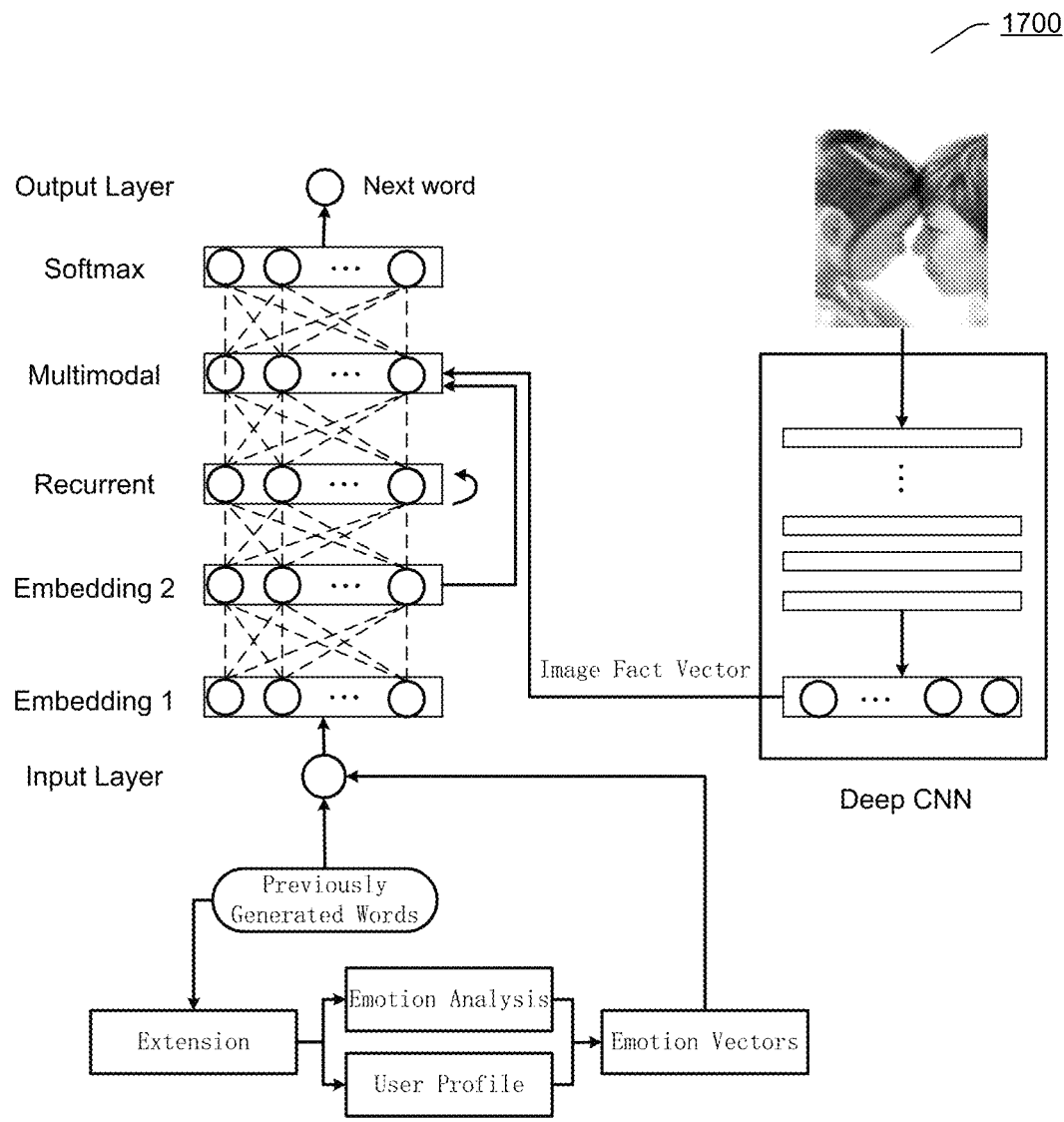
FIG. 17 illustrates an exemplary process for generating a textual description from an image according to an embodiment.

FIG. 17 illustrates an exemplary process 1700 for generating a textual description from an image according to an embodiment. For example, the textual description may be generated through neural networks in a word-by-word approach.

The process 1700 is based on a CNN-RNN framework, wherein the deep CNN in the right part of FIG. 17 may be used for obtaining a fact vector of an input image, and the RNN in the left part of FIG. 17 may be used for generating a text sentence, e.g., a textual description of the input image. The deep CNN in FIG. 17 may be based on the ResNet in FIG. 7. The fundamental idea of the process 1700 is to match an image and a text sentence in a latent semantic space, wherein the image is projected into a dense vector space through the deep CNN and the sentence is projected into another dense vector space through the RNN.

Training data for the process 1700 may be in a form of <image, text>. For example, an image of face-to-face communication between a mother and her daughter and a text sentence of "This photo was between me and my five-year-old daughter. When we communicate in a face-to-face way, I see her red and healthy face, and my tears just flow out" which describes the image may be used as an instance of training data, wherein the image is provided to the deep CNN and the text sentence is provided to the RNN. In some cases, sentences in the training data may be broken into words, and all the words may be extracted to form a vocabulary set. Then, words from different sentences may be recombined based on clues from an input image to form a new sentence which is optimized to fit the input image based on generation probabilities.

The sentence generation process in FIG. 17 may work as follows. The fact vector I of the input image is provided to a multimodal layer of the RNN. A softmax layer may compute probabilities of words in a target vocabulary set, and select at least one word with the maximum probability. In an implementation, beam search may be used for keeping record of the top-B candidate words, wherein B is the beam size. For example, when B is 3, it means that the first 3 words that have the highest probabilities are kept record in the softmax layer.

One or more previously generated words $\{w_1, w_2, \ldots, w_{i-1}\}$, as a generated part of the text sentence, may be input through an input layer of the RNN. A vector w(t) may be obtained through embedding layers 1 and 2 of the RNN. A vector r(t) may be obtained through a recurrent layer of the RNN. The vectors w(t) and r(t) together with the fact vector I of the input image may be provided to the multimodal layer as three input vectors. These three input vectors may be added together at the multimodal layer through:

$$m(t) = g(V_w * w(t) + V_r * r(t) + V_I * I) \qquad \text{Equation (14)}$$

wherein, "+" denotes element-wise addition, m denotes the multimodal layer feature vector, g(x) is an element-wise scaled hyperbolic tangent function, and $g(x) = 1.7159 * \tanh(2x/3)$. The function g(x) forces gradients into the most non-linear value range and leads to a faster training process than a basic hyperbolic tangent function.

Based on outputs from the multimodal layer, the softmax layer will select a next word or top-B possible next words from the vocabulary set.

The above generating process may be iteratively performed, and may stop as far as a </s> symbol which denotes the ending of a text sentence.

It should be appreciated that, the above process 1700 is exemplary, and various variants or improvements may be made in the process 1700.

In an implementation, a semantic extension operation may be applied on the generated part of the textual description, e.g., the previously generated words. The semantic extension operation may be used for extending the generated part so as to enrich diversity of the textual description. The semantic extension operation may be based on at least one of fact information in the user profile, and knowledge information in a knowledge graph. For example, the fact information in the user profile may comprise information about topics, actions, locations, times, etc. When determining that one of the previously generated words is associated with topics in at least one fact information item in the fact information of the user profile, this previously generated word may be semantically extended based on this fact information item. Moreover, for example, the knowledge graph may comprise knowledge information in certain domains, e.g., disease, food, medicine, or in any general domains, and the knowledge information may be represented by, such as, <topic1, topic2, relation>. When determining that one of the previously generated words is associated with a piece of knowledge information in the knowledge graph, this previously generated word may be semantically extended based on this piece of knowledge information.

In an implementation, after applying the semantic extension operation, emotion information, e.g., an emotion vector, may be obtained for each of the previously generated words or its extended words. Hereinafter, "a previously generated word" may refer to both the previously generated word itself and any extended words obtained for this previously generated word. In one approach, an emotion vector of a previously generated word may be obtained through performing emotion analysis on this previously generated word. In another approach, an emotion vector of a previously generated word may be obtained through emotion information of the user profile. For example, an emotion information item in the user profile may comprise topic, opinion, and emotion category. When determining that the previously generated word is associated with a topic in an emotion information item in the user profile, an emotion category in this emotion information item may be deemed as an emotion category of this previously generated word. Then, an emotion vector of this previously generated word may be formed based on the emotion category.

It should be appreciated that an emotion vector for a previously generated word may be obtained through either or both of the above emotion analysis-based approach and the above user profile-based approach. In the case of obtaining the emotion vector for the previously generated word through both of the emotion analysis-based approach and the user profile-based approach, this emotion vector may be a concatenation of emotion vectors obtained through these two approaches respectively. Moreover, it should be appreciated that although the above discussion involves the semantic extension operation, this operation may also be omitted from the process 1700.

Emotion vectors for the previously generated words obtained as mentioned above may be provided to the input layer together with fact vectors of the previously generated words, wherein the fact vectors may be obtained through applying word2vec techniques on the previously generated words. Thus, for each previously generated word, its dense vector representation may be formed by a concatenation of fact vector and emotion vector. In this way, the next word of the textual description may be generated in FIG. 17 based on at least one of: emotion information in the user profile that is associated with a generated part of the textual description; and emotion information obtained through performing emotion analysis on the generated part of the textual description. The final textual description would be an emotional description which may follow the user's emotions. For example, as for an input image showing a plurality of spicy dishes, if the user profile indicates that the user has a positive emotion on spicy foods, the process 1700 would generate a textual description for the input image in a positive way, such as, "You've eaten so many delicious spicy dishes". However, if the user profile indicates that the user has a negative emotion on spicy foods, the process 1700 would generate a textual description for the input image in a negative way, such as, "Too much spicy foods are not good for healthy".

The textual description for the image obtained through the process 1700 in FIG. 17 may be further used for creating a memory record.

Figure 18:
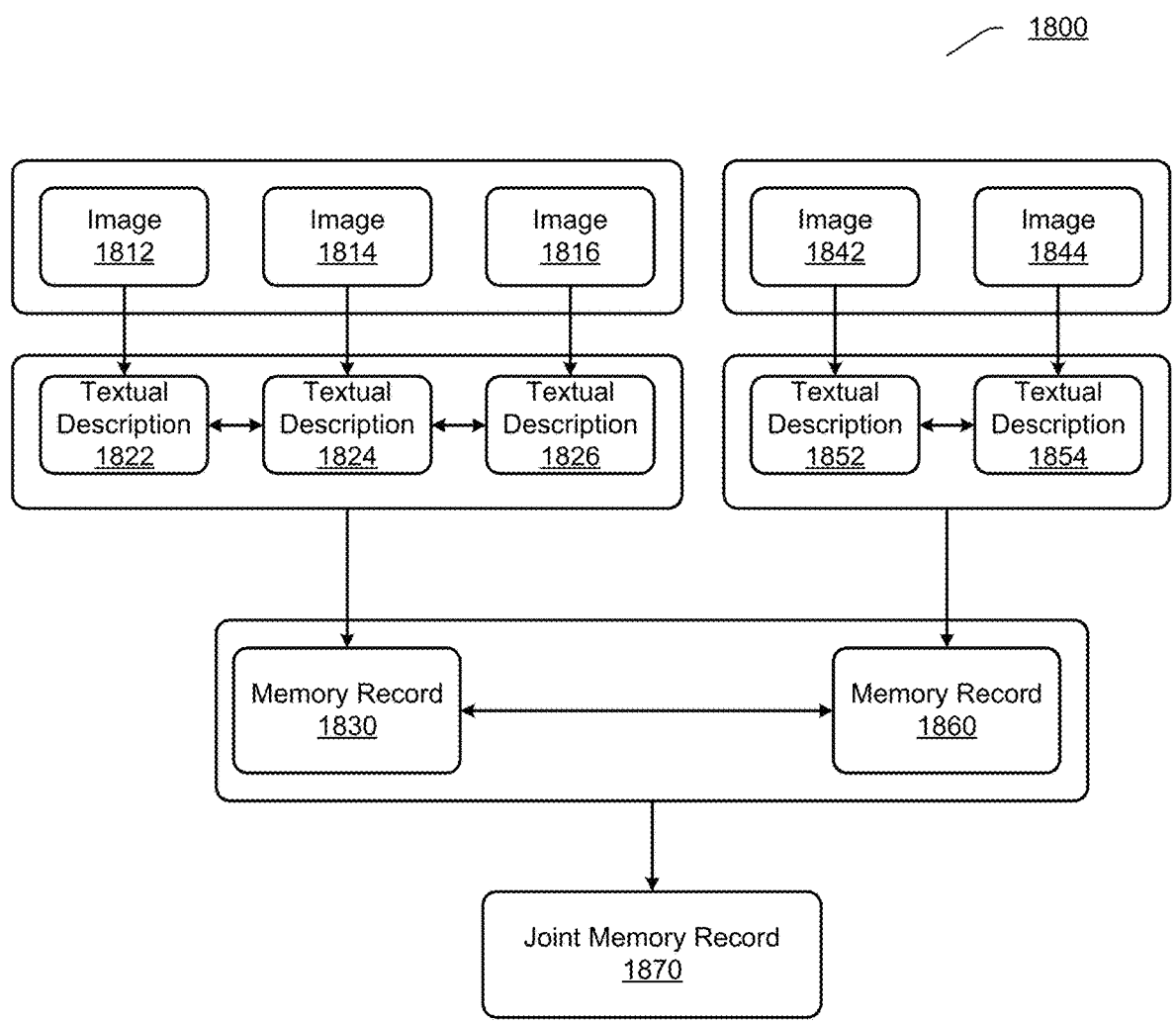
FIG. 18 illustrates an exemplary process for creating memory records according to an embodiment.

FIG. 18 illustrates an exemplary process 1800 for creating memory records according to an embodiment.

A first group of images, e.g., an image 1812, an image 1814 and an image 1816, may be received in a session between a chatbot and a user. For example, the user may share the first group of images with the chatbot in the session. Then, a first group of textual descriptions may be generated from the first group of images according to the process 1700 in FIG. 17, which may comprise a textual description 1822 corresponding to the image 1812, a textual description 1824 corresponding to the image 1814, and a textual description 1826 corresponding to the image 1816.

In the case that the first group of images is associated with the same topic, a memory record 1830 may be created based at least on the first group of images and the first group of textual descriptions. The memory record 1830 may link the first group of textual descriptions together, and thus the memory record 1830 may be like a "story" describing the user's experiences shown in the first group of images. In an implementation, if relationship between two textual description is obscure, the chatbot may try to determine the relationship through an inquiry way. Taking the textual description 1824 and the textual description 1826 as an example, if the textual description 1824 is about "Climb a hill by bike" and the textual description 1826 is about "Enjoy lake landscape", in order to find out relationship between these two scenarios described in the textual description 1824 and the textual description 1826 respectively, the chatbot may generate a question for inquiring relationship between the textual description 1824 and the textual description 1826, e.g., "Did you go to the lake by bike after climbing the hill?", and provide the question to the user. The question may be generated based on the textual description 1824 and the textual description 1826 through a sequence-to-sequence deep learning model. Then, the chatbot may receive an answer from the user which indicates the relationship, such as, "Yes, I ride my bike from the hill to the lake". Accordingly, based on the relationship determined above, the chatbot may create a memory record from the textual description 1824 and the textual description 1826, such as, "You climb a hill by bike, and then ride to the lake to enjoy the lake landscape".

As shown in FIG. 18, a second group of images including an image 1842 and an image 1844 may also be received by the chatbot. The first group of images and the second group of images may be sorted by time and/or location. A second group of textual descriptions including a textual description 1852 and a textual description 1854 may be generated from the second group of images. Then a memory record 1860 may be created based at least on the second group of images and the second group of textual descriptions.

In an implementation, the chatbot may try to link the memory record 1830 and the memory record 1860 together to create a joint memory record 1870, wherein the joint memory record 1870 may be like a list of "stories" describing the user's experiences shown in both the first group of images and the second group of images.

In the case that relationship between the memory record 1830 and the memory record 1860 is obscure, the chatbot may try to determine the relationship through an inquiry way. Assuming that the memory record 1830 is related to the user's travel to Singapore and the memory record 1860 is related to the user's travel to Malaysia, the chatbot may generate a question for inquiring relationship between the memory record 1830 and the memory record 1860, e.g., "Did you travel from Singapore to Malaysia?", and provide the question to the user. The question may be generated based on the memory record 1830 and the memory record 1860 through a sequence-to-sequence deep learning model. If the chatbot receives an answer "Yes" from the user which confirms the chatbot's assumption of the relationship, the chatbot may further create the joint memory record 1870 which describes the user's experiences in a travel both Singapore and Malaysia.

It should be appreciated that all the operations in the process 1800 are exemplary, and the embodiments of the present invention are not limited to any detailed operations in the process 1800. For example, more or less images may be included in the first or second group of images, the memory record 1830 and the memory record 1860 may be stored in a memory record database independently instead of further creating the joint memory record 1870, etc.

Figure 19:
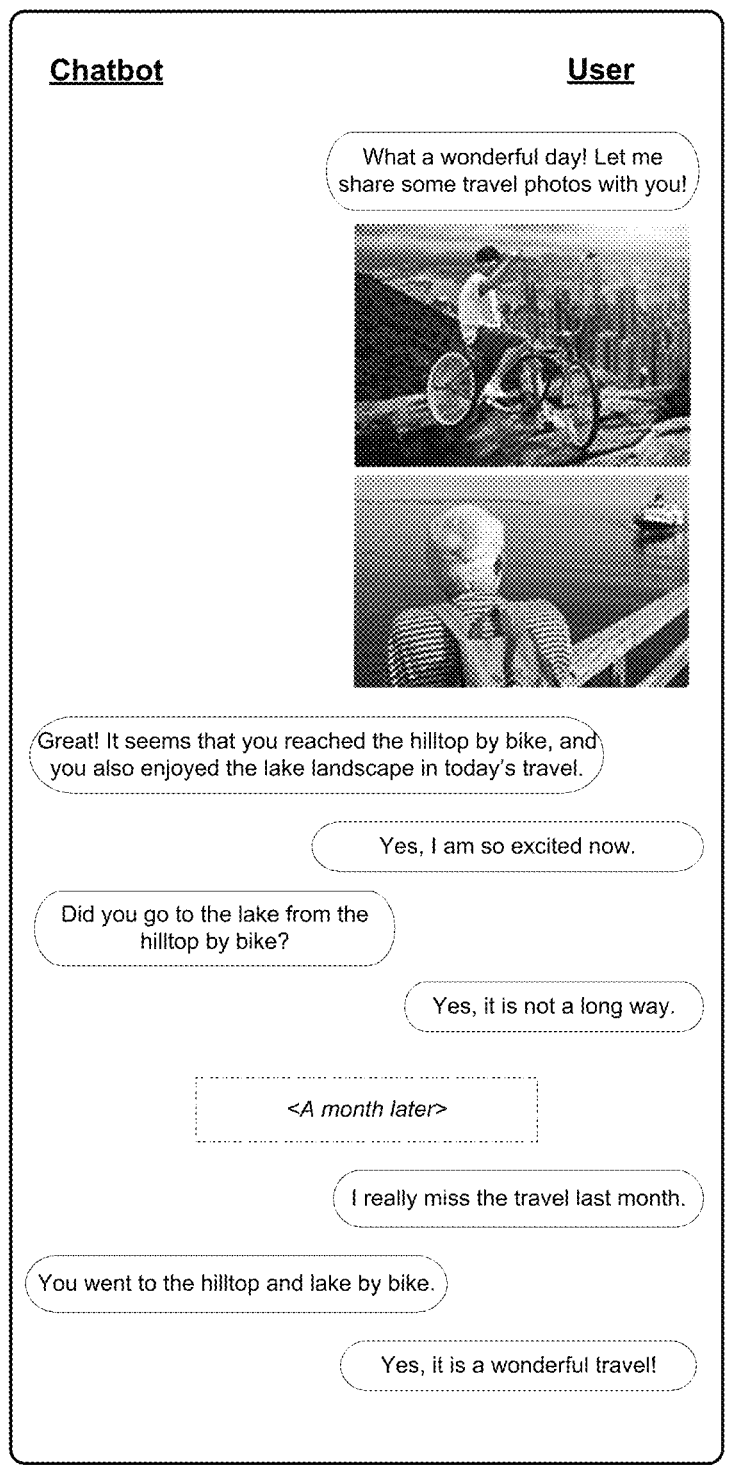
FIG. 19 illustrates an exemplary chat window according to an embodiment.

FIG. 19 illustrates an exemplary chat window 1900 according to an embodiment. The chat window 1900 shows a chat flow in which the chatbot may create and retrieve memory records according to the process 1700 in FIG. 17 and the process 1800 in FIG. 18.

After inputting a message "What a wonderful day! Let me share some travel photos with you!" by a user in a session, the user may further upload two photos. The chatbot may generate a first textual description "You reached the hilltop by bike" from the first photo and a second textual description "You enjoyed the lake landscape" from the second photo respectively according to the process 1700 in FIG. 17. The chatbot may provide a response based on the first textual description and the second textual description, such as "Great! It seems that you reached the hilltop by bike, and you also enjoyed the lake landscape in today's travel". Since both the photos are associated with the user's travel today, the chatbot may try to further create a memory record based on the first textual description and the second textual description. The chatbot may generate a question "Did you go to the lake from the hilltop by bike?" so as to inquire relationship between the first textual description and the second textual description. After receiving an answer "Yes, it is not a long way" from the user, the chatbot may determine that the relationship between the first textual description and the second textual description is riding bike to the hilltop firstly and then riding bike to the lake to enjoy the lake landscape, and accordingly the chatbot may create a memory record about the user's travel to the hilltop and the lake by bike. The memory record may be stored in a memory record database.

After a month later, when the user sends a message "I really miss the travel last month", the chatbot may try to help the user to recall the experience in the travel. For example, the chatbot may retrieve the memory record that is associated with the travel from the memory record database, and provide a response "You went to the hilltop and lake by bike" accordingly.

According to the embodiments of the present invention, the chatbot may monitor the user's psychological or cognitive conditions through conducting psychological or cognitive tests in a session. The psychological or cognitive tests may be conducted in an explicit way or in an implicit way.

Figure 20:
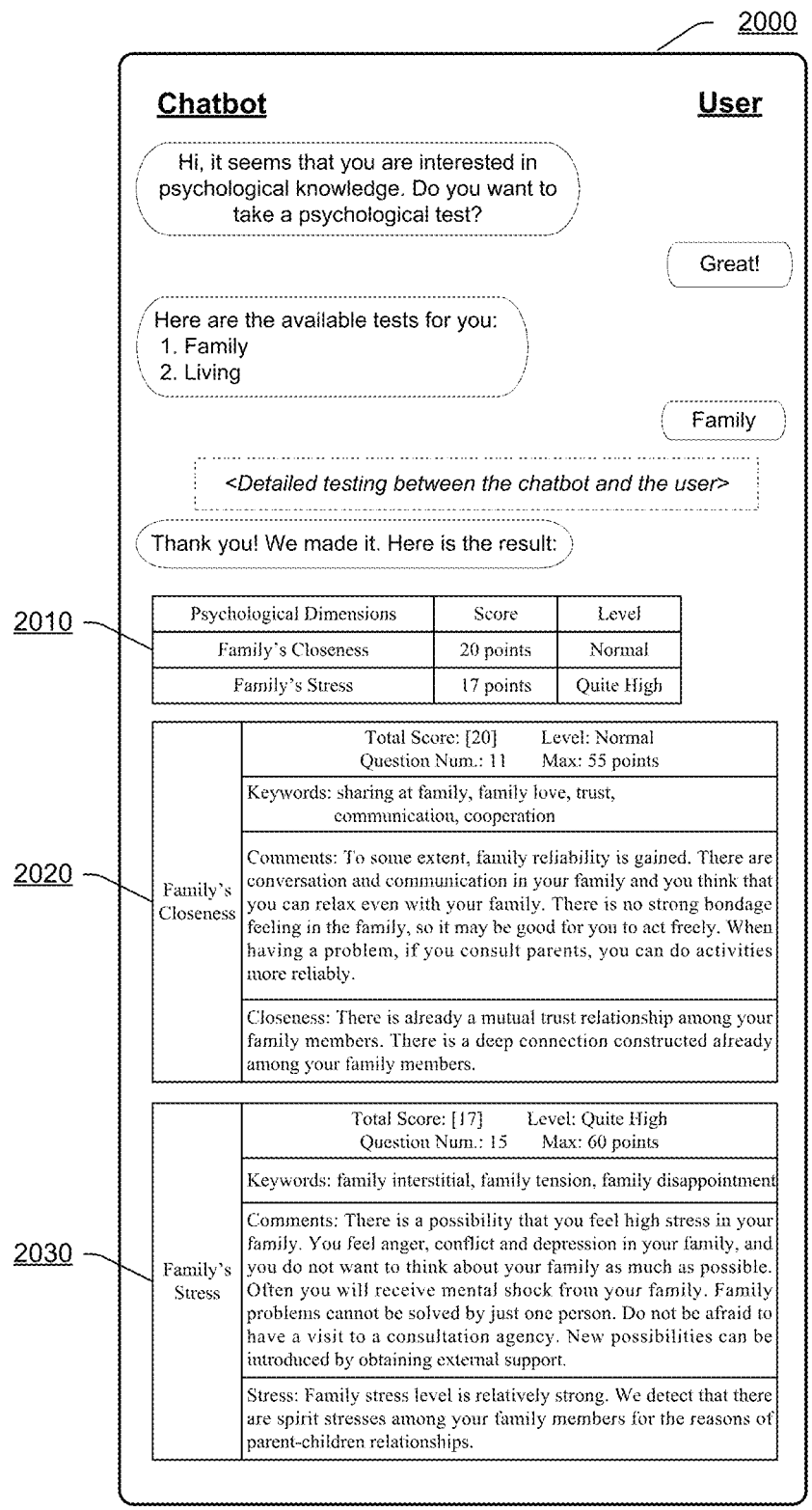
FIG. 20 illustrates an exemplary chat window according to an embodiment.

FIG. 20 illustrates an exemplary chat window 2000 between a chatbot and a user according to an embodiment. The chat window 2000 shows a procedure of performing an explicit psychological test. The explicit psychological test may also be referred to as a formatted psychological test, and may comprise a plurality of psychological questions and reference answers that are predetermined artificially or automatically. There may be various types of explicit psychological tests that belong to various psychological domains, e.g., "Family", "Living", etc.

An explicit psychological test may be determined to be performed if the user explicitly requires a psychological test by inputting a message, e.g., "I want to take a psychological test". Moreover, an explicit psychological test may also be determined to be performed if the user inputs a message including a positive response, e.g., "Yes", to a question, e.g., "Do you want to take a psychological test?" from the chatbot. An example of the latter is shown in the chat window 2000. However, it should be appreciated that the chat flow in the chat window 2000 is exemplary, and the embodiments of the present invention are not limited to any detailed expressions or procedures in the chat window 2000.

As shown in the chat window 2000, when the chatbot asks "Do you want to take a psychological test?", the user inputs a message "Great!" as a reply. The chatbot may determine, based on the message input by the user, that the user accepts to take a psychological test, and thus an explicit psychological test may be conducted.

The chatbot may provide the user with two options, e.g., "Family" and "Living", that belong to different psychological domains. When the user chooses "Family", the chatbot may begin to conduct an explicit psychological test in a "Family" domain. During the test, the chatbot may send psychological questions to the user, and receive the user's answers. An exemplary psychological question may be "Do you talk with your family these days?", and an exemplary answer "Yes, I talked with my family frequently" may be received from the user.

The chatbot may score the user's answers based on a scoring algorithm predefined by psychologists or experts in psychological domains, and may provide a test result of the psychologist test. As shown in FIG. 20, the test result may comprise a summarization part 2010. The summarization part 2010 may comprise one or more psychological dimensions which indicate types of the test result, e.g., family's closeness and family's stress, and scores and levels obtained by the user in the psychological dimensions. The test result may further comprise detailed information of the psychological dimensions, e.g., the family's closeness part 2020 and the family's stress part 2030. Taking the family's closeness part 2020 as an example, it comprises: basic information item, including total score, level, question numbers and maximum score; keywords item, including one or more top-ranked keywords extracted from the questions in the test; comments item, including detailed analysis on the user's performance in terms of the family's closeness; and closeness item, including a brief conclusion on the user's performance in terms of the family's closeness. Regarding the comments item, it may be generated based on the user's answers to the questions in the test and a list of keywords in the questions through a sequence-to-sequence deep learning model. Regarding the closeness item, a classifier may be used for classifying the user's answers to one of a plurality of predefined levels, and a predefined brief conclusion corresponding to the matched level may be retrieved and shown in the closeness item.

It should be appreciated that all the parts and items in the test result in FIG. 20 are exemplary, and according to actual applications and requirements, more or less parts and items may be included in the test result. Moreover, the form of the test result is not limited to a table, but may be in any other forms, such as, charts, plain texts, etc.

It should be appreciated that, in an implementation, the test result may be generated based on not only the user's answers, but also answers from at least one another user that is associated with the user. For example, when the user is taking a "Family" psychological test, if the user's family members also have taken the test or a relevant test before, then the test result may be generated based on answers from both the user and his family members. For example, the comments item may be generated based on the user's answers to the questions in the test, a list of keywords in the questions in the test, another list of keywords in questions in a test taken by the user's family members, and the user's family member's answers. Thus, a more precise and thorough evaluation on the user may be achieved because of that both the user's performance and his family members' performances are considered.

Figure 21:
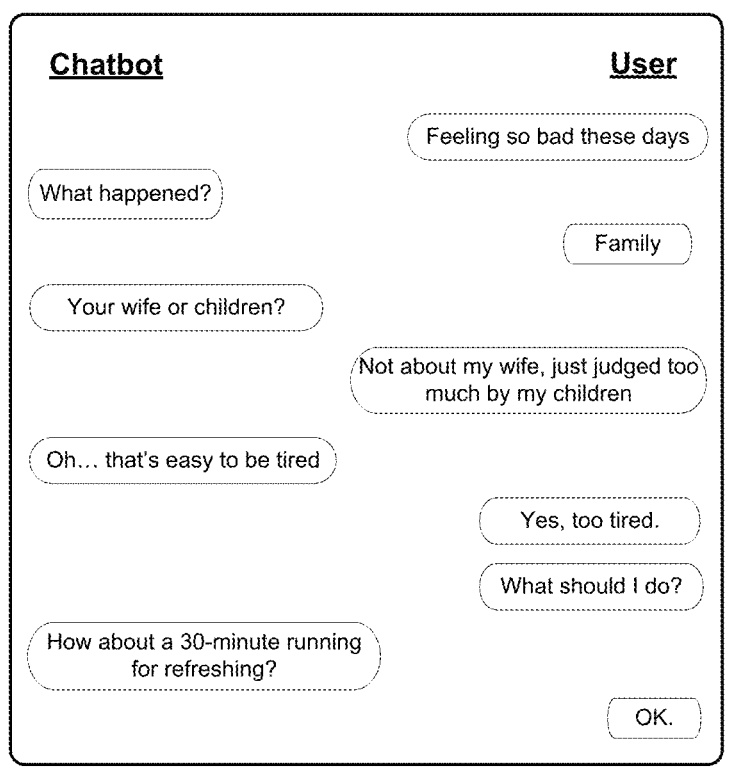
FIG. 21 illustrates an exemplary chat window according to an embodiment.

FIG. 21 illustrates an exemplary chat window 2100 between a chatbot and a user according to an embodiment. The chat window 2100 shows a procedure of performing an implicit psychological test. The implicit psychological test may refer to performing a psychological test in an implicit way, such as, sending psychological questions and receiving the user's answers in a session of a chat flow in a way that is not recognizable for the user. In some cases, it is important to perform the implicit psychological test, for the purpose of not taking too much time of the user, or avoiding that the user answers in an imaginary or fake way when the user is told to take a psychological test.

In an implementation, the psychological questions in the implicit psychological test may be generated based on transformation of psychological questions in a formatted psychological test as mentioned in FIG. 20, where the transformation of psychological questions in the formatted psychological test may intend to express the psychological questions in an implicit way.

In an implementation, the psychological questions in the implicit psychological test may be generated based on at least one of: occurrence frequencies of topics in the user profile; and an answer from the user to a previous question. In one aspect, candidate questions in the implicit psychological test may be ranked based on occurrence frequencies of topics in the user profile, and those candidate questions corresponding to topics of high occurrence frequencies may be selected to provide to the user, thus the questions most relevant to the user or likely to be interested by the user may be included in the test and may encourage the user to answer the questions instead of avoiding them. In another aspect, a next question in the implicit psychological test may be determined dynamically based on an answer from the user to a previous question. In this case, mutex criteria may be applied in the selection of the next question so as to avoid selecting a mutex question. Herein, a mutex question may refer to a question for which an answer would be determinate if an answer to a previous question is given. For example, if an answer "No" is given for a previous question "Do you like to see movies?", then a question "Do you like Hollywood movies?" would be a mutex question because in the condition that the user does not like to see movies, it is certain that the user would not like Hollywood movies. Moreover, for example, if an answer "Yes, I play football every week" is given for a previous question "Do you play football?", then a question "Do you do exercise frequently?" would be a mutex question because in the condition that the user plays football very week, it is certain that the user must do exercise frequently. Multilayer Perceptron (MLP) may be used for classification of mutex questions. Features in the MLP may comprise at least one of term frequency vector and engineering feature vector. The term frequency vector may be based on bag of words, and the engineering feature vector may be based on, such as, BM2.5, word2vec distance, edit distance, etc.

As shown in the chat window 2100, when the user inputs a message "Feeling so bad these days", the chatbot may determine that the user is in a negative emotion. Thus, the chatbot may further try to perform an implicit psychological test. For example, the chatbot may ask "What happened?" so as to start the implicit psychological test.

When receiving an answer "Family" from the user, the chatbot may further ask a question "Your wife or children?" which is generated in a psychological "Family" domain for determining reasons of the negative emotion of the user.

The user may answer by "Not about my wife, just judged too much by my children". Thus, the chatbot may acknowledge that the user has the negative emotion because of interpersonal relationship, e.g., being judged too much by the children.

The chatbot may further send a response "Oh . . . that's easy to be tired" so as to confirm body reactions of the user. Then, the user may input a message "Yes, too tired" which confirms that the user feels tired in terms of body reactions.

When the user asks "What should I do?", the chatbot may give a suggestion "How about a 30-minute running for refreshing?".

As discussed above, the chatbot may learn the user's psychological conditions from answers of the user received in the session of the chat flow.

It should be appreciated that the implicit psychological test in the chat window 2100 is exemplary, and the embodiments of the present invention are not limited to any detailed expressions or procedures in the chat window 2100.

Moreover, although not shown in FIG. 21, it should be appreciated that a result of the implicit psychological test may be generated by the chatbot, which may be in a form as shown in FIG. 20 or in any other forms. Alternatively, the result of the implicit psychological test may also be presented to the user.

Figure 22:
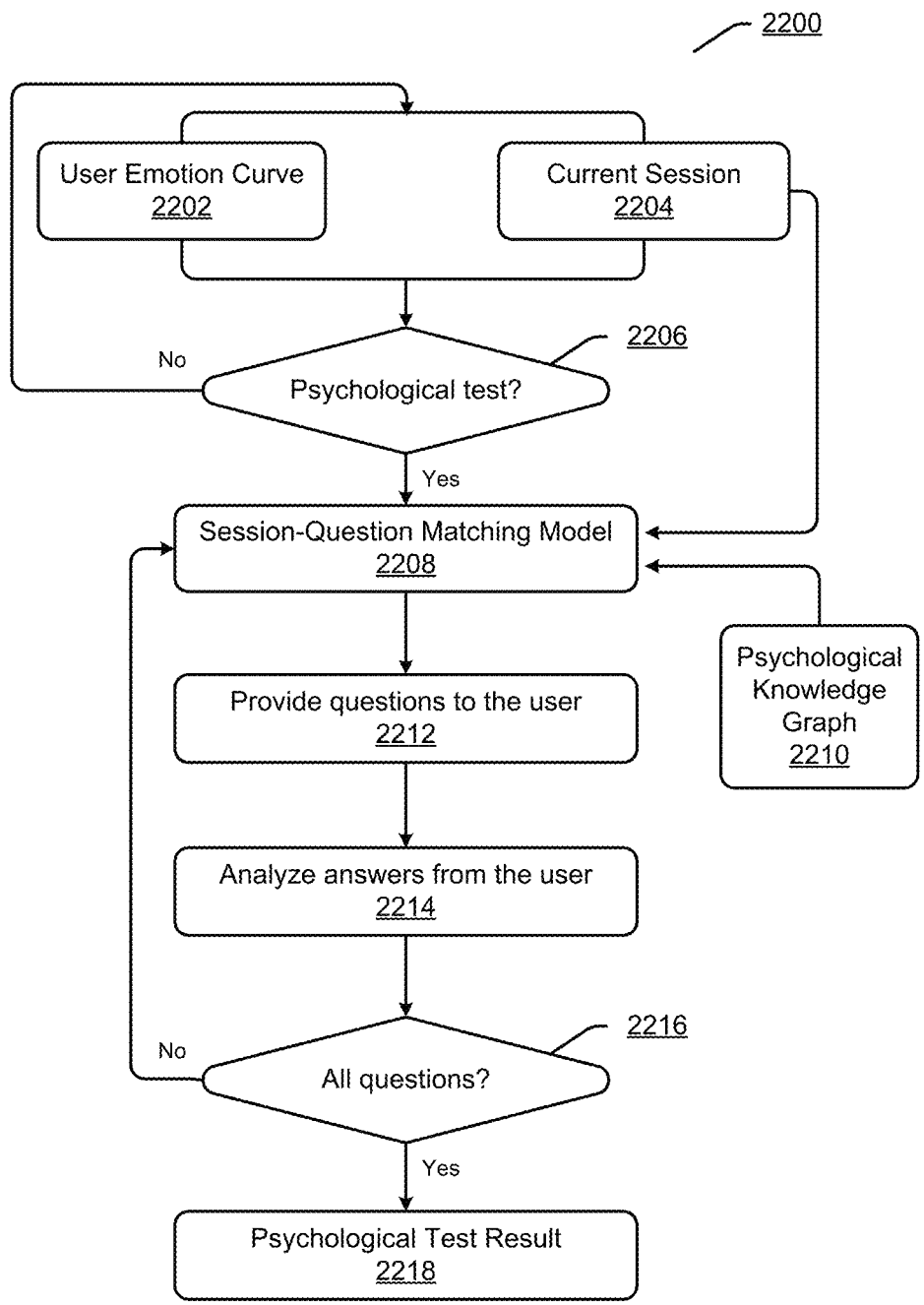
FIG. 22 illustrates an exemplary process for performing an implicit psychological test according to an embodiment.

FIG. 22 illustrates an exemplary process 2200 for performing an implicit psychological test according to an embodiment.

In some cases, the process 2200 may be triggered by an emotion curve 2202 of a user. If the current emotion state of the user is judged as below a predetermined threshold on the emotion curve, then it is determined at 2206 that an implicit psychological test may be performed.

In other cases, the process 2200 may be triggered by a current session 2204 of the user. For example, if messages input by the user in the current session is judged, through emotion analysis, as having negative emotions, then it is determined at 2206 that an implicit psychological test may be performed.

If it is determined at 2206 that no psychological test is required to be performed, the process 2200 may return so as to further judge the emotion curve 2202 and the current session 2204.

When determining to perform an implicit psychological test, a session-question matching model may be used at 2208 for determining psychological questions in the implicit psychological test based at least on the current session 2204 and a psychological knowledge graph 2210.

Taking the chat flow in FIG. 21 as an example, when the user inputs "Feeling so sad these days", the current session may be denoted as: Session 1="User: Feeling so sad these days". A question "What happened?" may be determined by the session-question matching model as a psychological question in the psychological test. When the user inputs "Family", the current session may be updated as: Session 2="User: Feeling so sad these days; Chatbot: What happened?; User: Family". A further question "Your wife or children?" may be determined by the session-question matching model as a further psychological question in the psychological test.

As discussed above, the session-question matching model may decide which question to be shown to the user, so as to further capture the user's opinion or answer for psychological condition detecting.

A gradient-boosting decision tree (GBDT) may be adopted in the session-question matching model to compute similarity scores between the current session 2204 and questions in psychological data pairs in the psychological knowledge graph 2210, wherein these psychological data pairs may be QA-style psychological data pairs, and questions in the psychological data pairs may also be referred to as candidate questions. Features in the GBDT may be based on at least one of a language model for information retrieval, a translation-based language model, an edit distance between a candidate question and a current session in a word or character level, a maximum subsequence ratio between a candidate question and a current session, a cosine similarity score between a candidate question and a current session. Moreover, as mentioned above, the questions in the implicit psychological test may be generated further based on at least one of: occurrence frequencies of topics in the user profile; and an answer from the user to a previous question.

Through the session-question matching model, one or more psychological questions may be determined for the psychological test. At 2212, the psychological questions may be provided to the user.

At 2214, answers from the user may be analyzed. For example, an emotion analysis process according to the embodiments of the present disclosure may be applied on the answers from the user, so as to detect the user's current psychological condition or emotion state.

At 2216, it may be determined whether all psychological questions in the psychological test have been sent to the user. If not, the process 2200 may return to 2208. If yes, a psychological test result may be generated at 2218. The psychological test result may be in various forms, such as, the test result shown in FIG. 20, etc.

It should be appreciated that, although not shown in FIG. 22, there may be a test control strategy included in the process 2200. For example, if there are a lot of psychological questions needed to be sent to the user so as to obtain a final result, the process 2200 may record questions that the user has answered, questions remaining to be sent to the user, and time duration of the psychological test having been conducted. Thus, the whole psychological test may be conducted in several parts in two or more sessions, rather than conducted at a time.

It should be appreciated that although explicit and implicit psychological tests are discussed above in connection with FIG. 20-FIG. 22, explicit and implicit cognitive tests may also be conducted in a similar way. The difference is that, in a psychological test, it is more about emotional responses to psychological questions and emotional answers can be scored by emotion analysis, while in a cognitive test, it is more about reasoning or computing abilities, in which answers are determinate and a direct comparison between the user's answers and standard answers may be made to evaluate the user's cognitive ability without the need of utilizing emotion analysis. For example, for a cognitive question "What the result of (5*3+2*4)", for which a standard answer should be "23", if the user's answer is "23" then the user may gain a score for this question, otherwise the user would not gain a score for this question.

Figure 23:
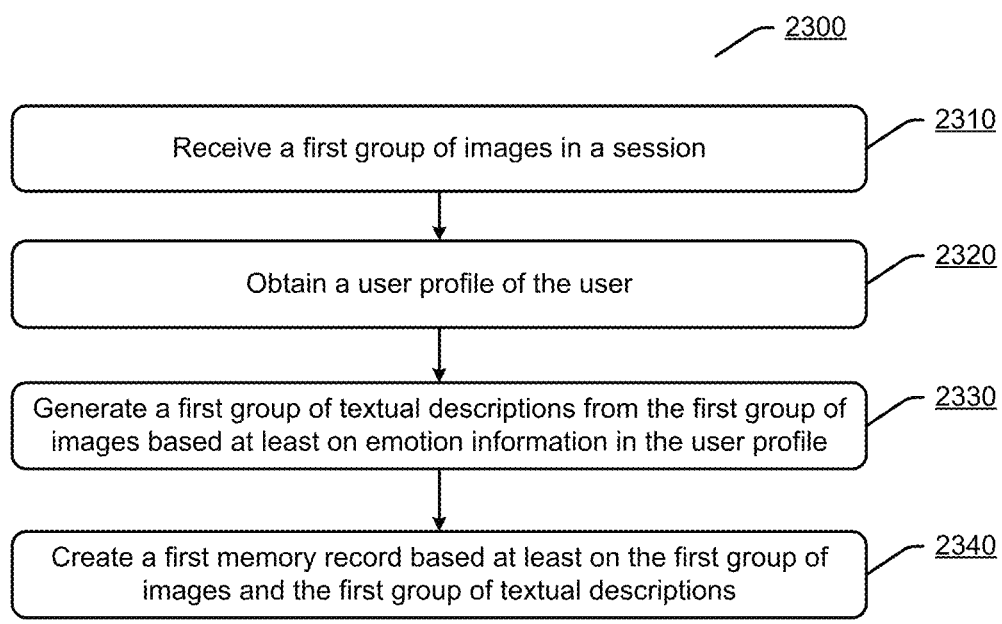
FIG. 23 illustrates a flowchart of an exemplary method for providing emotional care in a session between a user and an electronic conversational agent according to an embodiment.

FIG. 23 illustrates a flowchart of an exemplary method 2300 for providing emotional care in a session between a user and an electronic conversational agent according to an embodiment.

At 2310, a first group of images may be received in the session, the first group of images comprising one or more images associated with the user.

At 2320, a user profile of the user may be obtained.

At 2330, a first group of textual descriptions may be generated from the first group of images based at least on emotion information in the user profile.

At 2340, a first memory record may be created based at least on the first group of images and the first group of textual descriptions.

In an implementation, the method 2300 may further comprise: providing a response in the session based on the first memory record.

In an implementation, the method 2300 may further comprise: storing the first memory record in a memory record database, the memory record database including a plurality of memory records. In an implementation, the method 2300 may further comprise: receiving a message in the session; retrieving a memory record associated with the message from the memory record database; and providing a response in the session based on the retrieved memory record.

In an implementation, the first group of textual descriptions may comprise a first textual description corresponding to a first image and a second textual description corresponding to a second image. The creating the first memory record may comprise: generating a question for inquiring relationship between the first textual description and the second textual description; providing the question in the session; receiving an answer indicating the relationship in the session; and creating the first memory record based at least on the relationship.

In an implementation, the method 2300 may further comprise: receiving a second group of images in the session; generating a second group of textual descriptions from the second group of images based at least on the emotion information in the user profile; and creating a second memory record based at least on the second group of images and the second group of textual descriptions. In an implementation, the method 2300 may further comprise: generating a question for inquiring relationship between the first memory record and the second memory record; providing the question in the session; receiving an answer indicating the relationship in the session; and creating a joint memory record based at least on the first memory record, the second memory record and the relationship.

In an implementation, each of the first group of textual descriptions may be generated through neural networks in a word-by-word approach.

In an implementation, during generating a textual description, a next word of the textual description may be generated based on at least one of: emotion information in the user profile that is associated with a generated part of the textual description; and emotion information obtained through performing emotion analysis on the generated part of the textual description. The emotion information in the user profile may comprise a plurality of emotion information items, and each emotion information item may comprise at least one of: a topic of interest, opinion on the topic, and emotion category of the opinion.

In an implementation, during generating a textual description, a generated part of the textual description may be semantically extended by at least one of: fact information in the user profile, and knowledge information in a knowledge graph. The fact information in the user profile may comprise a plurality of fact information items, and each fact information item may comprise at least one of: a topic of interest, action, location and time.

In an implementation, the method 2300 may further comprise: performing a psychological test or a cognitive test in the session. Each of questions in the psychological test or the cognitive test may be determined based on at least one of: an answer from the user to a previous question, and occurrence frequencies of topics in the user profile. Each of questions in the psychological test or the cognitive test may be determined based on mutex criteria. A test result of the psychological test or cognitive test may be determined based on answers from the user and/or answers from at least one another user that is associated with the user.

It should be appreciated that the method 2300 may further comprise any steps/processes for providing emotional care in a session according to the embodiments of the present disclosure as mentioned above.

Figure 24:
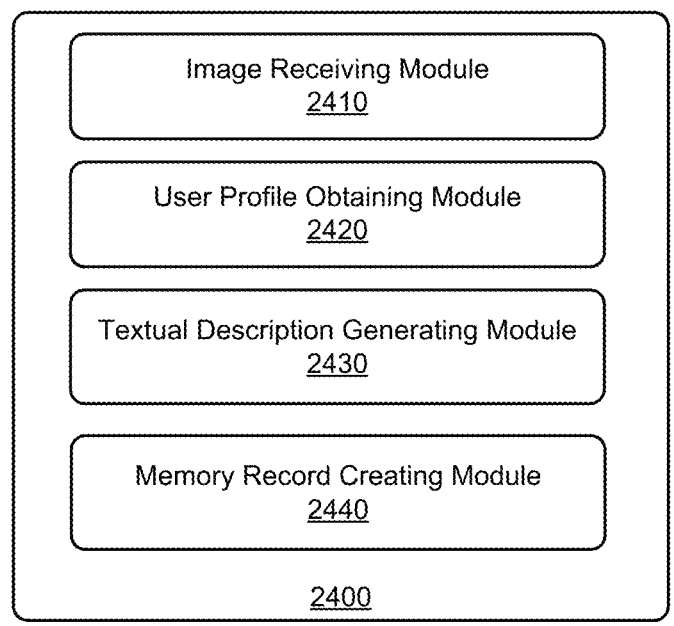
FIG. 24 illustrates an exemplary apparatus for providing emotional care in a session between a user and an electronic conversational agent according to an embodiment.

FIG. 24 illustrates an exemplary apparatus 2400 for providing emotional care in a session between a user and an electronic conversational agent according to an embodiment.

The apparatus 2400 may comprise: an image receiving module 2410, for receiving a first group of images in the session, the first group of images comprising one or more images associated with the user; a user profile obtaining module 2420, for obtaining a user profile of the user; a textual description generating module 2430, for generating a first group of textual descriptions from the first group of images based at least on emotion information in the user profile; and a memory record creating module 2440, for creating a first memory record based at least on the first group of images and the first group of textual descriptions.

In an implementation, the first group of textual descriptions may comprise a first textual description corresponding to a first image and a second textual description corresponding to a second image. The memory record creating module 2440 may be further for: generating a question for inquiring relationship between the first textual description and the second textual description; providing the question in the session; receiving an answer indicating the relationship in the session; and creating the first memory record based at least on the relationship.

In an implementation, each of the first group of textual descriptions may be generated through neural networks in a word-by-word approach. During generating a textual description, a next word of the textual description may generated based on at least one of: emotion information in the user profile that is associated with a generated part of the textual description; and emotion information obtained through performing emotion analysis on the generated part of the textual description.

Moreover, the apparatus 2400 may also comprise any other modules configured for providing emotional care in a session according to the embodiments of the present disclosure as mentioned above.

Figure 25:
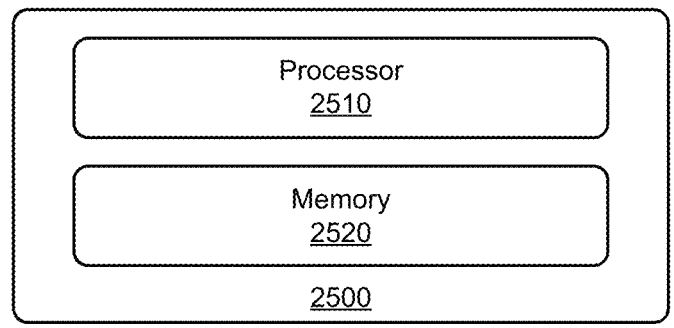
FIG. 25 illustrates an exemplary apparatus for providing emotional care in a session between a user and an electronic conversational agent according to an embodiment.

FIG. 25 illustrates an exemplary apparatus 2500 for providing emotional care in a session between a user and an electronic conversational agent according to an embodiment.

The apparatus 2500 may comprise one or more processors 2510 and a memory 2520 storing computer-executable instructions. When executing the computer-executable instructions, the one or more processors 2510 may: receive a first group of images in the session, the first group of images comprising one or more images associated with the user; obtain a user profile of the user; generate a first group of textual descriptions from the first group of images based at least on emotion information in the user profile; and create a first memory record based at least on the first group of images and the first group of textual descriptions. The one or more processors 2510 may be further configured for performing any operations of the methods for providing emotional care in a session according to the embodiments of the present disclosure as mentioned above.

The embodiments of the present disclosure may be embodied in a non-transitory computer-readable medium. The non-transitory computer-readable medium may comprise instructions that, when executed, cause one or more processors to perform any operations of the methods for providing emotional care in a session according to the embodiments of the present disclosure as mentioned above.

It should be appreciated that all the operations in the methods described above are merely exemplary, and the present disclosure is not limited to any operations in the methods or sequence orders of these operations, and should cover all other equivalents under the same or similar concepts.

It should also be appreciated that all the modules in the apparatuses described above may be implemented in various approaches. These modules may be implemented as hardware, software, or a combination thereof. Moreover, any of these modules may be further functionally divided into sub-modules or combined together.

Processors have been described in connection with various apparatuses and methods. These processors may be implemented using electronic hardware, computer software, or any combination thereof. Whether such processors are implemented as hardware or software will depend upon the particular application and overall design constraints imposed on the system. By way of example, a processor, any portion of a processor, or any combination of processors presented in the present disclosure may be implemented with a microprocessor, microcontroller, digital signal processor (DSP), a field-programmable gate array (FPGA), a programmable logic device (PLD), a state machine, gated logic, discrete hardware circuits, and other suitable processing components configured to perform the various functions described throughout the present disclosure. The functionality of a processor, any portion of a processor, or any combination of processors presented in the present disclosure may be implemented with software being executed by a microprocessor, microcontroller, DSP, or other suitable platform.

Software shall be construed broadly to mean instructions, instruction sets, code, code segments, program code, programs, subprograms, software modules, applications, software applications, software packages, routines, subroutines, objects, threads of execution, procedures, functions, etc. The software may reside on a computer-readable medium. A computer-readable medium may include, by way of example, memory such as a magnetic storage device (e.g., hard disk, floppy disk, magnetic strip), an optical disk, a smart card, a flash memory device, random access memory (RAM), read only memory (ROM), programmable ROM (PROM), erasable PROM (EPROM), electrically erasable PROM (EEPROM), a register, or a removable disk. Although memory is shown separate from the processors in the various aspects presented throughout the present disclosure, the memory may be internal to the processors, e.g., cache or register.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein. All structural and functional equivalents to the elements of the various aspects described throughout the present disclosure that are known or later come to be known to those of ordinary skill in the art are expressly incorporated herein by reference and are intended to be encompassed by the claims.

What is claimed is:

1. A method for providing emotional care in a session between a user and an electronic conversational agent, comprising:
   receiving a first group of images in the session, the first group of images comprising one or more images associated with the user;
   obtaining a user profile of the user;
   generating a first group of textual descriptions from the first group of images based at least on emotion information in the user profile;
   creating a first memory record based at least on the first group of images and the first group of textual descriptions;
   performing at least one of: an implicit psychological test and an explicit psychological test in the session; and
   notifying the user when an implicit psychological test is performed to obtain permission from the user to perform the implicit psychological test.

2. The method of claim 1, further comprising:
   notifying the user when an explicit psychological test is performed to obtain permission from the user to perform the explicit psychological test and providing the user with the alternative to perform the implicit psychological test if the user prefers the implicit psychological test over the explicit psychological test.

3. The method of claim 1, further comprising:
   providing a response in the session based on the first memory record.

4. The method of claim 1, further comprising:
   storing the first memory record in a memory record database, the memory record database including a plurality of memory records.

5. The method of claim 4, further comprising:
   receiving a message in the session;
   retrieving a memory record associated with the message from the memory record database; and
   providing a response in the session based on the retrieved memory record.

6. The method of claim 1, wherein each of the first group of textual descriptions is generated through neural networks in a word-by-word approach.

7. The method of claim 6, wherein during generating a textual description, a next word of the textual description is generated based on at least one of: emotion information in the user profile that is associated with a generated part of the textual description; and emotion information obtained through performing emotion analysis on the generated part of the textual description.

8. The method of claim 7, wherein the emotion information in the user profile comprises a plurality of emotion information items, and each emotion information item comprises at least one of: a topic of interest, opinion on the topic, and emotion category of the opinion.

9. The method of claim 6, wherein during generating a textual description, a generated part of the textual description is semantically extended by at least one of: fact information in the user profile, and knowledge information in a knowledge graph.

10. The method of claim 9, wherein the fact information in the user profile comprises a plurality of fact information items, and each fact information item comprises at least one of: a topic of interest, action, location and time.

11. A method for providing emotional care in a session between a user and an electronic conversational agent, comprising:
    receiving a first group of images in the session, the first group of images comprising one or more images associated with the user;
    obtaining a user profile of the user;
    generating a first group of textual descriptions from the first group of images based at least on emotion information in the user profile;
    creating a first memory record based at least on the first group of images and the first group of textual descriptions; and
    performing a psychological test or a cognitive test in the session.

12. The method claim 11, wherein each of questions in the psychological test or the cognitive test is determined based on at least one of: an answer from the user to a previous question, and occurrence frequencies of topics in the user profile.

13. The method claim 12, wherein each of questions in the psychological test or the cognitive test is determined based on mutex criteria.

14. The method claim 11, wherein a test result of the psychological test or cognitive test is determined based on answers from the user and/or answers from at least one another user that is associated with the user.

15. An apparatus for providing emotional care in a session between a user and an electronic conversational agent, comprising:
    one or more processors; and
    a memory storing computer-executable instructions that, when executed, cause the one or more processors to:
    receive a first group of images in the session, the first group of images comprising one or more images associated with the user;

obtain a user profile of the user;

generate a first group of textual descriptions from the first group of images based at least on emotion information in the user profile;

create a first memory record based at least on the first group of images and the first group of textual descriptions;

perform at least one of: an implicit psychological test and an explicit psychological test in the session; and notify the user when an implicit psychological test is performed to obtain permission from the user to perform the implicit psychological test.

16. The apparatus of claim 15, wherein memory storing computer-executable instructions that, when executed, further cause the one or more processors to:

notify the user when an explicit psychological test is performed to obtain permission from the user to perform the explicit psychological test and provide the user with the alternative to perform the implicit psychological test if the user prefers the implicit psychological test over the explicit psychological test.

17. The apparatus of claim 16, wherein during generating a textual description, a next word of the textual description is generated based on at least one of: emotion information in the user profile that is associated with a generated part of the textual description; and emotion information obtained through performing emotion analysis on the generated part of the textual description.

18. The apparatus of claim 17, wherein the emotion information in the user profile comprises a plurality of emotion information items, and each emotion information item comprises at least one of: a topic of interest, opinion on the topic, and emotion category of the opinion.

19. The apparatus of claim 16, wherein during generating a textual description, a generated part of the textual description is semantically extended by at least one of: fact information in the user profile, and knowledge information in a knowledge graph.

20. The apparatus of claim 15, wherein each of the first group of textual descriptions is generated through neural networks in a word-by-word approach.

* * * * *